US008466099B2

(12) United States Patent
Glenn, Jr. et al.

(10) Patent No.: US 8,466,099 B2
(45) Date of Patent: *Jun. 18, 2013

(54) PROCESS OF MAKING AN ARTICLE FOR DISSOLUTION UPON USE TO DELIVER SURFACTANTS

(75) Inventors: Robert Wayne Glenn, Jr., Liberty Twp., OH (US); John Philip Hecht, West Chester, OH (US); Jason Donald McCarty, Wilmington, OH (US); Raul Victorino Nunes, Loveland, OH (US); Mark William Hamersky, Indian Springs, OH (US); Elizabeth Anne Wilder, West Chester, OH (US); James Merle Heinrich, Fairfield, OH (US); Darren Paul Trokhan, Hamilton, OH (US); Thomas Edward Dufresne, Morrow, OH (US); Julie Masters Lubbers, Fort Thomas, KY (US); Renee Danielle Bolden, Hamilton, OH (US); Lee Arnold Schechtman, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/633,228

(22) Filed: Dec. 8, 2009

(65) Prior Publication Data

US 2010/0298188 A1     Nov. 25, 2010

Related U.S. Application Data

(60) Provisional application No. 61/120,637, filed on Dec. 8, 2008.

(51) Int. Cl.
*C11D 11/00*     (2006.01)
*B29C 44/00*     (2006.01)

(52) U.S. Cl.
USPC .............. 510/445; 510/455; 510/457; 264/50

(58) Field of Classification Search
USPC .............................. 510/445, 455, 457; 264/50
See application file for complete search history.

(56) References Cited

U.S. PATENT DOCUMENTS

| | | | |
|---|---|---|---|
| 2,356,168 A | 8/1941 | Mabley | |
| 2,396,278 A | 3/1946 | Lind | |
| 2,438,091 A | 3/1948 | Lynch | |
| 2,486,921 A | 11/1949 | Byerly | |
| 2,486,922 A | 11/1949 | Strain | |
| 2,528,378 A | 10/1950 | Mannheimer et al. | |
| 2,658,072 A | 11/1953 | Kosmin | |
| 2,694,668 A | 11/1954 | Fricke | |
| 2,809,971 A | 10/1957 | Bernstein | |
| 3,152,046 A | 10/1964 | Kapral | |
| 3,236,733 A | 2/1966 | Karsten | |
| 3,321,425 A | 5/1967 | Blau et al. | |
| 3,332,880 A | 7/1967 | Kessler | |
| 3,426,440 A * | 2/1969 | Shen et al. | ........................ 34/368 |
| 3,489,688 A * | 1/1970 | Pospischil | ..................... 510/135 |
| 3,653,383 A | 4/1972 | Wise | |
| 3,695,989 A | 10/1972 | Albert | |
| 3,753,196 A | 8/1973 | Kurtz | |
| 3,761,418 A | 9/1973 | Parran, Jr. | |
| 3,929,678 A | 12/1975 | Laughlin | |
| 3,967,921 A * | 7/1976 | Haberli et al. | .................... 8/477 |
| 4,020,156 A | 4/1977 | Murray | |
| 4,051,081 A | 9/1977 | Jabs et al. | |
| 4,089,945 A | 5/1978 | Brinkman | |
| 4,196,190 A | 3/1980 | Gehman | |
| 4,197,865 A | 4/1980 | Jacquet | |
| 4,217,914 A | 8/1980 | Jacquet | |
| 4,272,511 A | 6/1981 | Papantoniou | |
| 4,323,683 A | 4/1982 | Bolich, Jr. | |
| 4,345,080 A | 8/1982 | Bolich, Jr. | |
| 4,379,753 A | 4/1983 | Bolich, Jr. | |
| 4,381,919 A | 5/1983 | Jacquet | |
| 4,422,853 A | 12/1983 | Jacquet | |
| 4,470,982 A | 9/1984 | Winkler | |
| 4,507,280 A | 3/1985 | Pohl | |
| 4,529,586 A | 7/1985 | De Marco | |
| 4,565,647 A | 1/1986 | Llenado | |
| 4,663,158 A | 5/1987 | Wolfram | |
| 4,710,374 A | 12/1987 | Grollier | |
| 4,822,613 A | 4/1989 | Rodero | |
| 4,885,107 A | 12/1989 | Wetzel | |
| 4,976,953 A | 12/1990 | Orr | |
| 4,990,280 A | 2/1991 | Thorengaard et al. | |
| 5,055,384 A | 10/1991 | Kuhnert | |
| 5,061,481 A | 10/1991 | Suzuki | |
| 5,062,889 A | 11/1991 | Hohl et al. | |
| 5,094,853 A | 3/1992 | Hagarty | |
| 5,100,657 A | 3/1992 | Ansher-Jackson | |
| 5,100,658 A | 3/1992 | Bolich, Jr. | |
| 5,104,646 A | 4/1992 | Bolich, Jr. | |
| 5,106,609 A | 4/1992 | Bolich, Jr. | |

(Continued)

FOREIGN PATENT DOCUMENTS

| | | |
|---|---|---|
| CN | 1138091 | 12/1996 |
| CN | 1219388 A | 6/1999 |

(Continued)

OTHER PUBLICATIONS

T. Hildebrand, P. Rüegsegger. Quantification of bone microarchitecture with the structure model index. *Comp Meth Biomech Biomed Eng* 1997; 1:15-23.

(Continued)

*Primary Examiner* — Lorna M Douyon
(74) *Attorney, Agent, or Firm* — Angela K. Haughey

(57) ABSTRACT

A process that results in a flexible dissolvable porous solid article that can be used as a personal care composition or a fabric care composition.

13 Claims, 12 Drawing Sheets

U.S. PATENT DOCUMENTS

| | | |
|---|---|---|
| 5,166,276 A | 11/1992 | Hayama |
| 5,220,033 A | 6/1993 | Kamei et al. |
| 5,280,079 A | 1/1994 | Allen |
| RE34,584 E | 4/1994 | Grote |
| 5,391,368 A | 2/1995 | Gerstein |
| 5,409,703 A | 4/1995 | McAnalley |
| 5,429,628 A | 7/1995 | Trinh |
| 5,457,895 A | 10/1995 | Thompson et al. |
| 5,476,597 A | 12/1995 | Sakata et al. |
| 5,580,481 A | 12/1996 | Sakata et al. |
| 5,582,786 A | 12/1996 | Brunskill |
| 5,660,845 A | 8/1997 | Trinh |
| 5,672,576 A | 9/1997 | Behrens |
| 5,674,478 A | 10/1997 | Dodd |
| 5,750,122 A | 5/1998 | Evans |
| 5,780,047 A | 7/1998 | Kamiya et al. |
| 5,955,419 A | 9/1999 | Barket, Jr. |
| 6,010,719 A | 1/2000 | Remon |
| 6,106,849 A * | 8/2000 | Malkan et al. ................ 424/401 |
| 6,177,391 B1 | 1/2001 | Zafar |
| 6,200,949 B1 | 3/2001 | Reijmer |
| 6,458,754 B1 | 10/2002 | Velazquez |
| 6,503,521 B1 | 1/2003 | Atis et al. |
| 6,790,814 B1 | 9/2004 | Marin |
| 6,846,784 B2 | 1/2005 | Engel et al. |
| 6,943,200 B1 | 9/2005 | Corrand et al. |
| 7,015,181 B2 | 3/2006 | Lambino |
| 7,285,520 B2 | 10/2007 | Krzysik et al. |
| 7,901,696 B2 | 3/2011 | Eknoian |
| 8,268,764 B2 * | 9/2012 | Glenn et al. ................ 510/120 |
| 8,273,333 B2 * | 9/2012 | Glenn et al. ................ 424/70.11 |
| 8,288,332 B2 * | 10/2012 | Fossum et al. ................ 510/440 |
| 8,309,505 B2 * | 11/2012 | Fossum et al. ................ 510/235 |
| 8,349,341 B2 * | 1/2013 | Glenn et al. ................ 424/401 |
| 8,349,786 B2 * | 1/2013 | Glenn et al. ................ 510/298 |
| 8,349,787 B2 * | 1/2013 | Glenn et al. ................ 510/298 |
| 2002/0064510 A1 | 5/2002 | Dalrymple |
| 2002/0077264 A1 | 6/2002 | Roberts et al. |
| 2002/0081930 A1 | 6/2002 | Jackson et al. |
| 2002/0098994 A1 | 7/2002 | Zafar |
| 2002/0099109 A1 | 7/2002 | Dufton et al. |
| 2002/0177621 A1 | 11/2002 | Hanada |
| 2002/0187181 A1 | 12/2002 | Godbey et al. |
| 2003/0032573 A1 * | 2/2003 | Tanner et al. ................ 510/400 |
| 2003/0045441 A1 | 3/2003 | Hsu et al. |
| 2003/0069154 A1 | 4/2003 | Hsu et al. |
| 2003/0080150 A1 | 5/2003 | Cowan et al. |
| 2003/0099691 A1 | 5/2003 | Lydzinski |
| 2003/0099692 A1 | 5/2003 | Lydzinski et al. |
| 2003/0180242 A1 | 9/2003 | Eccard et al. |
| 2003/0186826 A1 * | 10/2003 | Eccard et al. ................ 510/130 |
| 2003/0194416 A1 | 10/2003 | Shefer |
| 2003/0199412 A1 | 10/2003 | Gupta |
| 2003/0207776 A1 | 11/2003 | Shefer |
| 2003/0215522 A1 | 11/2003 | Johnson |
| 2003/0232183 A1 | 12/2003 | Dufton |
| 2004/0029762 A1 | 2/2004 | Hensley |
| 2004/0032859 A1 | 2/2004 | Miao |
| 2004/0048759 A1 * | 3/2004 | Ribble et al. ................ 510/141 |
| 2004/0053808 A1 * | 3/2004 | Raehse et al. ................ 510/447 |
| 2004/0071742 A1 | 4/2004 | Popplewell |
| 2004/0071755 A1 | 4/2004 | Fox |
| 2004/0108615 A1 | 6/2004 | Foley |
| 2004/0110656 A1 | 6/2004 | Casey |
| 2004/0126585 A1 | 7/2004 | Kerins et al. |
| 2004/0175404 A1 | 9/2004 | Shefer |
| 2004/0202632 A1 | 10/2004 | Gott |
| 2004/0206270 A1 | 10/2004 | Vanmaele |
| 2004/0242772 A1 | 12/2004 | Huth et al. |
| 2005/0069575 A1 | 3/2005 | Fox |
| 2005/0118237 A1 | 6/2005 | Krzysik et al. |
| 2005/0136780 A1 | 6/2005 | Clark et al. |
| 2005/0137272 A1 | 6/2005 | Gaserod et al. |
| 2005/0202992 A1 | 9/2005 | Grandio Portabales |
| 2005/0220745 A1 | 10/2005 | Lu |
| 2005/0232954 A1 | 10/2005 | Yoshinari |
| 2005/0272836 A1 | 12/2005 | Yaginuma et al. |
| 2005/0287106 A1 | 12/2005 | Legendre |
| 2006/0002880 A1 | 1/2006 | Peffly |
| 2006/0052263 A1 | 3/2006 | Roreger |
| 2006/0228319 A1 | 10/2006 | Vona, Jr. et al. |
| 2007/0028939 A1 | 2/2007 | Mareri et al. |
| 2007/0149435 A1 | 6/2007 | Koenig |
| 2007/0225388 A1 | 9/2007 | Cooper et al. |
| 2008/0035174 A1 | 2/2008 | Aubrun-Sonneville et al. |
| 2008/0090939 A1 | 4/2008 | Netravali et al. |
| 2008/0131695 A1 | 6/2008 | Aouad |
| 2008/0138492 A1 | 6/2008 | Cingotti |
| 2008/0152894 A1 | 6/2008 | Beihoffer |
| 2008/0215023 A1 | 9/2008 | Scavone |
| 2008/0293839 A1 | 11/2008 | Stobby |
| 2009/0232873 A1 * | 9/2009 | Glenn et al. ................ 424/443 |
| 2009/0263342 A1 * | 10/2009 | Glenn et al. ................ 424/70.11 |
| 2010/0167971 A1 | 7/2010 | Glenn, Jr. |
| 2010/0173817 A1 | 7/2010 | Glenn, Jr. |
| 2010/0179083 A1 | 7/2010 | Glenn, Jr. |
| 2010/0279905 A1 | 11/2010 | Glenn, Jr. |
| 2010/0286011 A1 | 11/2010 | Glenn, Jr. |
| 2010/0291165 A1 | 11/2010 | Glenn, Jr. |
| 2011/0023240 A1 | 2/2011 | Fossum |
| 2011/0028373 A1 | 2/2011 | Fossum |
| 2011/0028374 A1 | 2/2011 | Fossum |
| 2011/0182956 A1 | 7/2011 | Glenn, Jr. |
| 2011/0189246 A1 | 8/2011 | Glenn, Jr. |
| 2011/0189247 A1 | 8/2011 | Glenn, Jr. |
| 2011/0195098 A1 | 8/2011 | Glenn, Jr. |
| 2012/0021026 A1 | 1/2012 | Chhabra |

FOREIGN PATENT DOCUMENTS

| | | |
|---|---|---|
| CN | 1268558 A | 10/2000 |
| CN | 1357613 | 7/2002 |
| CN | 1530431 A | 9/2004 |
| CN | 1583991 A | 2/2005 |
| DE | 19607851 A1 | 9/1997 |
| DE | 10331767 A1 | 2/2005 |
| EP | 609808 A1 | 8/1994 |
| EP | 0858828 A1 | 8/1998 |
| EP | 1160311 B1 | 12/2001 |
| EP | 1217987 B1 | 12/2004 |
| EP | 2085434 A1 | 8/2009 |
| FR | 2871685 A | 12/2005 |
| FR | 2886845 A | 12/2006 |
| GB | 2235204 A | 2/1991 |
| GB | 2355008 A | 4/2001 |
| JP | 58021608 | 2/1983 |
| JP | 58216109 | 12/1983 |
| JP | 62-072609 | 4/1987 |
| JP | 62-072610 | 4/1987 |
| JP | 01313418 | 12/1989 |
| JP | 5344873 A | 12/1993 |
| JP | 6017083 A | 1/1994 |
| JP | 7089852 A | 4/1995 |
| JP | 1998325133 A | 12/1996 |
| JP | 10251371 A | 9/1998 |
| JP | 200373700 A | 3/2003 |
| JP | 200382397 | 3/2003 |
| JP | 2004345983 A | 12/2004 |
| JP | 2005171063 A | 6/2005 |
| JP | 2007197540 A | 8/2007 |
| JP | 2007091954 A | 12/2007 |
| KR | 2002-0003442 | 1/2002 |
| WO | WO9514495 A1 | 6/1995 |
| WO | WO01/24770 A1 | 4/2001 |
| WO | WO 2004/032859 A | 4/2004 |
| WO | WO2004/041991 A1 | 5/2004 |
| WO | WO2005/003423 A1 | 1/2005 |
| WO | WO2007033598 A1 | 3/2007 |
| WO | WO2007093558 | 8/2007 |
| WO | WO2009019571 | 2/2009 |

OTHER PUBLICATIONS

Vesterby, A.; Star volume in Bone Research a Histomorphometric Analysis of Trabecular Bone Structure Using Vertical Sections; Anat Rec.; Feb. 1993; 235(2):325-334.

ISR dated May 6, 2011, PCT/US2009/067130, 5 pages.

ISR dated May 4, 2011, PCT/US2009/067088, 5 pages.

ISR dated Jul. 19, 2011, PCT/US2009/067088, 7 pages.
ISR dated May 9, 2011, PCT/US2009/067132, 5 pages.
ISR dated Jul. 20, 2011, PCT/US2009/067131, 5 pages.
ISR dated Apr. 29, 2011, PCT/US2009/067089, 5 pages.
ISR dated Jul. 15, 2009, PCT/IB2009/050388, 8 pages.
ISR dated Aug. 17, 2009, PCT/US2009/040739, 6 pages.
ISR dated Nov. 4, 2009, PCT/US2009/040739, 10 pages.
ISR dated Dec. 15, 2011, PCT/US2009/067087, 5 pages.
ISR dated Jul. 19, 2011, PCT/US2009/067133, 4 pages.
ISR dated Jul. 19, 2011, PCT/US2009/067130, 7 pages.
ISR dated Apr. 27, 2011, PCT/US2010/059365, 5 pages.
ISR dated Apr. 27, 2011, PCT/US2010/059455, 5 pages.
ISR dated Apr. 27, 2011, PCT/US2010/059359, 5 pages.
C. D. Vaughan. Solubility, Effects in Product, Package, Penetration and Preservation, Cosmetics and Toiletries, vol. 103, Oct. 1988.
*Encyclopedia of Polymer Science and Engineering*, vol. 15, 2d ed., pp. 204-308, John Wiley & Sons, Inc. (1989).
Anonymous: "P8136 Poly(vinyl alcohol)" Internet article, [Online] XP002538935 Retrieved from the Internet: URL:http://www.sigmaaldrich.com/catalog/ProductDetail.do?D7=0 &N25=SEARCH_CONCAT_PNO%7CBRAND_KEY &N4=P8136%7CSIAL&N25=0&QS=0N&F=SPEC> [retrieved on Jul. 28, 2009].
*M. K. Industires* (Gujarat India, http://www.soapstrips.com).
*Sanipro Sanitary Products* (Italy, http://www.sanipro.it).
*Adhesives Research* (Pennsylvania, http://12.4.33.51/news/apresmed.htm).
*Solublon* (Toyohashi Japan, http://www.solublon.com).
*SPI Pharma* (Delaware, http://www.spipharma.com).
*Wenda* (China, http://www.wenda.com).
*MOVA Pharmaceutical and Kosmos* (USA, http://www.icon-pr.com/news/news_print.cfm?inv_id=266-1.
*Cima Labs, Inc.* (Minnesota, http://www.cimalabs.com/).
*Cardinal Health* (Dublin, Ohio, http://spd.cardinal.com/).
*Le Laboratoire du Bain* (France, http://www.labodubain.com/).
*Amerilab Technologies, Inc.* (Minnesota, http://www.amerilabtech.com/).
*Meguiar's Car Wash Strips:* (*Meguiar's Inc.* California, http://www.automotivedigest.com/view_art.asp?articlesID=12414).
*Pure Soap Leafz:* (*Soap UNLTD*, Netherlands, http://www.upandunder.co.uk/eshop/catalogue/testbs.asp?Manufacturer_ID=252&Activity_ID=33&Description_ID=157).
*Dissolving Soap Strips* (*Ranir LLC*, Michigan, www.ranir.com).
*Japanese Paper Soap* (http://www.wishingfish.com/papersoap.html).
*Travelers Passport Paper Soap Sheets* (http://www.weddingfavorsnow.com/index.asp?PageAction=VIEWPROD &ID=510).
Office Action for U.S. Appl. No. 12/424,812 dated Nov. 1, 2011; Glenn, Jr. et al.; filed Apr. 16, 2009.
Office Action for U.S. Appl. No. 12/633,257 dated Jun. 1, 2011; Glenn, Jr. et al.; filed Dec. 8, 2009.
Office Action for U.S. Appl. No. 12/633,257 dated Nov. 17, 2011; Glenn, Jr. et al.; filed Dec. 8, 2009.
Office Action for U.S. Appl. No. 12/633,301 dated Jun. 3, 2011; Glenn, Jr. et al.; filed Dec. 8, 2009.
Office Action for U.S. Appl. No. 12/633,301 dated Nov. 7, 2011; Glenn, Jr. et al.; filed Dec. 8, 2009.
Office Action for U.S. Appl. No. 12/633,550 dated Nov. 16, 2011; Glenn, Jr. et al.; filed Dec. 8, 2009.
Office Action for U.S. Appl. No. 12/633,335 dated Jul. 8, 2011; Glenn, Jr. et al.; filed Dec. 8, 2009.
Office Action for U.S. Appl. No. 12/633,415 dated Nov. 14, 2011; Glenn, Jr. et al.; filed Dec. 8, 2009.
Office Action for U.S. Appl. No. 12/633,572 dated Jul. 28, 2011; Glenn, Jr. et al.; filed Dec. 8, 2009.
Office Action for U.S. Appl. No. 12/361,634 dated Sep. 14, 2011; Glenn, Jr. et al.; filed Jan. 29, 2009.
U.S. Appl. No. 61/472,941, filed Apr. 7, 2011, Glenn, Jr.

* cited by examiner

Top cross-section   Middle cross-section   Bottom cross-section

Top cross-section   Bottom cross-section

Top cross-section   Middle cross-section   Bottom cross-section

Top cross-section   Middle cross-section   Bottom cross-section

Top cross-section    Middle cross-section    Bottom cross-section

Top cross-section    Middle cross-section    Bottom cross-section

Interior volume        Full volume

Interior volume    Full volume

Interior volume    Full volume

Interior volume    Full volume

Interior volume    Full volume

Interior volume        Full volume

Interior volume        Full volume

Interior volume     Full volume

Interior volume     Full volume

Interior volume        Full volume

Interior volume        Full volume

Interior volume          Full volume

Top cross-section    Middle cross-section    Bottom cross-section

Top cross-section    Middle cross-section    Bottom cross-section

Top cross-section    Middle cross-section    Bottom cross-section

Top cross-section    Middle cross-section    Bottom cross-section

Interior volume          Full volume

Interior volumeFull volume

Interior volumeFull volume

Interior volume    Full volume

Top cross-section    Middle cross-section    Bottom cross-section

Top cross-section    Middle cross-section    Bottom cross-section

Interior volume　　　　　　　　Full volume

Interior volume　　　　　　　　Full volume

PROCESS OF MAKING AN ARTICLE FOR DISSOLUTION UPON USE TO DELIVER SURFACTANTS

CROSS REFERENCE TO RELATE APPLICATION

This application claims the benefit of U.S. Provisional Application Ser. No. 61/120,637 filed Dec. 8, 2008, which is incorporated by reference herein.

FIELD OF THE INVENTION

The present invention relates to a process for making a flexible porous dissolvable solid structure article useful as a personal care product.

BACKGROUND OF THE INVENTION

Dissolvable personal care films are known comprising a water-soluble polymeric structurant and a surfactant or other active ingredient. However, in order to achieve the requisite rapid dissolution rates needed for consumer convenience, these films are generally on the order of less than 100 microns thickness (typically 50 microns) and, thereby, are generally of too low a basis weight (typically 50-100 grams of solid per square meter) to enable feasible consumer application of a sufficient dosage of active ingredients for entire body or whole head hair application and performance, i.e., beyond lower dosage applications such as hand cleansing and/or the facial applications.

Dissolvable porous solid personal care products have been taught comprising natural starch and surfactants (See US 2004/0048759). However, these porous solids were produced by an anhydrous extrusion process and employing volatile blowing agents to produce the cellular structure via high pressure drop induced expansion of the solid. The anhydrous process limits the components available to anhydrous materials such as solid-sourced surfactants which are unacceptably harsh to skin, hair and fabric surfaces and are known for "skin" formation due to the partial collapse of structure after the abrupt high pressure drop at the exit of the extruder die also termed "shrinkage". Such skins are unacceptable as these would serve as a barrier for water ingress to the interior and adversely affect dissolution rates.

Freeze-dried open-celled porous solids for personal care have been taught (See U.S. Pat. No. 6,106,849 and US 2007/0225388). However, such resulting freeze-dried porous solids are rigid, brittle and fragile and without plasticization of the polymer such that it remains in its glassy state to avoid collapse of the structure during the process (See U.S. Pat. No. 5,457,895 Kearney P. et. al., issued 1995). Also, freeze-drying is a relatively high energy and costly process.

Therefore a need exists for a process that results in a desired flexible, dissolvable porous solid structure which can be easily and quickly manufactured that gives the desired properties of flexibility, dissolution, surfactant dosing levels and lather by consumers utilizing such articles.

SUMMARY OF THE INVENTION

The present invention relates to a process for preparing a flexible porous dissolvable solid structure article, comprising the steps of: Preparing a pre-mixture comprising surfactant, water soluble polymer, and optionally plasticizer, wherein said pre-mixture comprises: from about 15% to 70% solids; and a viscosity of from about 2,500 cps to 150,000 cps; aerating said pre-mixture by introducing a gas into the pre-mixture to form a wet aerated pre-mixture; forming the wet aerated pre-mixture into a desired one or more shapes to formed aerated wet pre-mixture; and drying the formed aerated wet pre-mixture in a drying environment, wherein the drying environment is heated, such that the pre-mix is dried within about 3 minutes to about 90 minutes to a final moisture content from about 0.1% to about 25% moisture to form the flexible dissolvable porous solid structure article.

The present invention further relates to a process for preparing a porous dissolvable solid structure article, comprising the steps of: preparing a pre-mixture comprising surfactant, water soluble polymer, and optionally plasticizer, wherein said pre-mixture comprises: from about 30% to 70% solids; and ii. a viscosity of from about 15,000 cps to 150,000 cps; heating the pre-mixture between about 40° C. and about 99° C.; aerating said pre-mixture by introducing a gas into the pre-mixture to form a wet aerated pre-mixture; forming the wet aerated pre-mixture into a desired one or more shapes to formed aerated wet pre-mixture; and drying the shaped wet pre-mix to a dry density of from about 0.10 g/cm$^3$ to about 0.40 g/cm$^3$, to form the porous dissolvable solid structure article.

The present invention further relates to a process for preparing a flexible porous dissolvable solid structure article, comprising the steps of: Preparing a pre-mixture comprising surfactant, water soluble polymer, and optionally plasticizer, wherein said pre-mixture comprises: from about 30% to 70% solids; and a viscosity of from about 15,000 cps to 150,000; aerating said pre-mixture by introducing a gas into the pre-mixture to form a wet aerated pre-mixture; forming the wet aerated pre-mixture into a desired one or more shapes to formed aerated wet pre-mixture; and drying the formed aerated wet pre-mixture in a drying environment, wherein the drying environment is heated to a temperature between 100° C. and 150° C., such that the pre-mix is dried to a final moisture content from about 0.1% to about 25% moisture to form the flexible dissolvable porous solid structure article.

DETAILED DESCRIPTION OF THE INVENTION

Figure 1A:
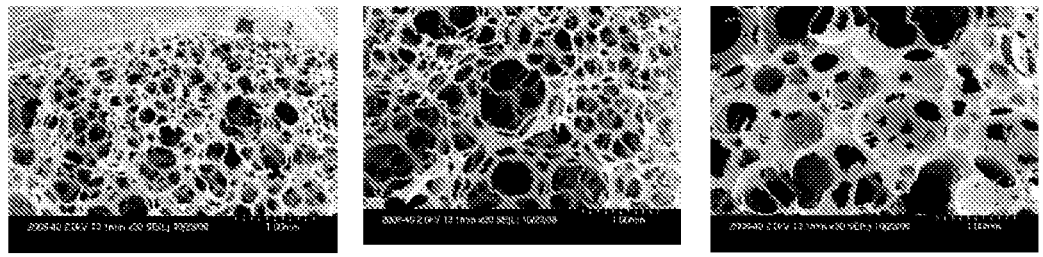
FIG. 1a SEM Images of Example 13.1.

The flexible porous dissolvable solid structure article may be referred to herein as "the Article" or "the Dissolvable Article". All references are intended to mean the flexible dissolvable porous solid structure article.

As used herein, "flexible" means that the porous dissolvable solid structure article meets the distance to maximum force values discussed herein.

The Article has a distance to maximum force value of from about 6 mm to about 30 mm, in one embodiment from about 7 mm to about 25 mm, in another embodiment from about 8 mm to about 20 mm, and in still another embodiment from about 9 mm to about 15 mm as measured by the Distance to Maximum Force Method.

As used herein, "dissolvable" means that the flexible porous dissolvable solid structure article meets the hand dissolution value. The Article has a hand dissolution value of from about 1 to about 30 strokes, in one embodiment from about 2 to about 25 strokes, in another embodiment from about 3 to about 20 strokes, and in still another embodiment from about 4 to about 15 strokes as measured by the Hand Dissolution Method.

As used herein "porous solid structure" means a solid, interconnected, polymer-containing matrix that defines a network of spaces or cells that contain a gas, typically a gas such as air without collapse of the foam structure during the drying process, thereby maintaining the physical strength and cohesiveness of the solid. The interconnectivity of the structure may be described by a Start Volume, a Structure Model Index (SMI) and a Percent Open Cell Content.

The Article has a Star Volume of from about 1 mm³ to about 90 mm³, in one embodiment from about 5 mm³ to about 80 mm³, in another embodiment from about 10 mm³ to about 70 mm³, and in still another embodiment from about 15 mm³ to about 60 mm³.

The Article has a non-negative Structure Model Index of from about 0.0 to about 3.0, in one embodiment from about 0.5 to about 2.75, and in another embodiment from about 1.0 to about 2.50.

To measure the cell interconnectivity via the Star Volume and the Structure Model Index, disk-like samples, approximately 4 cm in diameter and 3 to 7 mm high, are scanned using a micro computed tomography system (μCT80, SN 06071200, Scanco Medical AG). Each sample is imaged while sitting flat on the bottom of a cylindrical tube. Image acquisition parameters are 45 kVp, 177 μA, 51.2 mm field of view, 800 ms integration time, 1000 projections. The number of slices is adjusted to cover the height of the sample. The reconstructed data set consisted of a stack of images, each 2048×2048 pixels, with an isotropic resolution of 25 μm. For data analysis, a volume of interest is selected to be fully within the sample, avoiding the surface region. A typical volume of interest is 1028×772×98 voxels.

Structure Model Index (SMI) is measured using Scanco Medical's Bone Trabecular Morphometry evaluation with a threshold of 17. With this index the structural appearance of trabecular bone is quantified (see T. Hildebrand, P. Rüegsegger. Quantification of bone microarchitecture with the structure model index. *Comp Meth Biomech Biomed Eng* 1997; 1:15-23). The triangulated surface is dilated in normal direction by an infinitesimal amount, and the new bone surface and volume is calculated. By this, the derivative of the bone surface (dBS/dr) can be determined. The SMI is then represented by the equation:

$$SMI = 6 \cdot \frac{BV \cdot \frac{dBS}{dr}}{BS^2}$$

SMI relates to the convexity of the structure to a model type. Ideal (flat) plates have an SMI of 0 (no surface change with dilation of the plates), whereas ideal cylindrical rods have an SMI of 3 (linear increase in surface with dilation of rods). Round spheres have an SMI of 4. Concave structure gives negative dBS/dr, resulting in negative SMI values. Artificial boundaries at the edge of the volume of interest are not included in the calculation and thus suppressed.

In addition to the Scanco Medical Analysis, Star Volume measurements are made. Star Volume is a measure of the "openness" of the void space in a two phase structure. By choosing a random uniformly distributed set of points in the phase of interest (in this case the phase of interest is the void space or air), lines can be extended in random directions from each of these points. The lines are extended until they touch the foreground phase. The length of each of these lines is then recorded. The random points have a sampling of 10 in each direction (x/y/z) and at each point 10 random angles are chosen. If the line extends to the border of the ROI of interest that line is discarded (only accept lines that actually intersect with the foreground phase). The final equation is based upon the research entitled *Star Volume In Bone Research A Histomorphometric Analysis Of Trabecular Bone Structure Using Vertical Sections*; Vesterby, A.; Anat Rec.; 1993 February; 235(2):325-334.:

$$StarVolume = \frac{4}{3}\pi \cdot \frac{\sum dist^3}{N}$$

where "dist" is the individual distances and N is the number of lines examined.

The Article has a Percent Open Cell Content of from about 80% to 100%, in one embodiment from about 85% to about 97.5%, and in another embodiment from about 90% to about 95%.

The Percent Open Cell Content is measured via gas pycnometry. Gas pycnometry is a common analytical technique that uses a gas displacement method to measure volume accurately. Inert gases, such as helium or nitrogen, are used as the displacement medium. The sample of the Article is sealed in the instrument compartment of known volume, the appropriate inert gas is admitted, and then expanded into another precision internal volume. The pressure before and after expansion is measured and used to compute the sample Article volume. Dividing this volume into the sample Article weight gives the gas displacement density.

The Article produced according to the process discussed herein results in a more uniform and consistent structure through the thickness of the Article. Conventional processing techniques generally lead to open-celled porous structures comprising three distinct regions: an upper region that is closest to the target density (based on extrapolation from the wet processing density), a middle region with a significantly lower density and larger pores, and a bottom region with a higher density and thicker cell walls. While not being bound to theory, the central region's lower density and larger pore sizes are believed to be due to excessive drainage and bubble collapse during the drying process and thereby also contributing to the higher density and thicker cell walls of the bottom region due to gravity. Moreover, this latter, more dense, region is believed to serve as a rate limiting barrier for water ingress into the porous solid upon being wetted by the consumer which significantly decreases the dissolution performance.

As such, the process described herein is directed to addressing these issues.

Method of Manufacture

The Article can be prepared by the process comprising: (1) Preparing a pre-mixture comprising surfactant(s), dissolved water soluble polymer, and optionally plasticizer and other optional ingredients; (2) Aerating the mixture by introducing a gas into the mixture; (3) Forming the aerated wet mixture into a desired thickness with optionally a three-dimensional mold; (4) Drying the aerated wet mixture to a desired final moisture content (e.g., from about 0.5 to 25% moisture), in an environment that is held at about 100° C. to about 150° C.; and (5) optionally cutting the dried solid into one or more shapes.

Preparation of Pre-Mixture

The pre-mixture is generally prepared by mixing the solids of interest, including surfactant(s), dissolved water soluble polymer, optional plasticizer and other optional ingredients. This can be accomplished by any suitable mixing processes such as batch or continuous mixing. High shear or static mixing is also suitable. Any process can be envisioned such that the polymer is ultimately dissolved in the presence of water, the surfactant(s), optional actives, optional plasticizer, and any other optional ingredients including step-wise processing via pre-mix portions of any combination of ingredients. The viscosity of the pre-mixture should fall within the ranges discussed herein at ambient temperatures (25° C.) and the percent solid content should fall within the ranges discussed herein.

Optional Continued Heating of Pre-Mixture

Optionally, the pre-mixture is pre-heated immediately prior to the aeration process at above ambient temperature but below any temperatures that would cause degradation of the component. In one embodiment, the pre-mixture is kept at above about 40° C. and below about 99° C., preferably above about 50° C. and below about 95° C., more preferably about 60° C. and below about 90° C. In one embodiment, when the viscosity at ambient temperature of the pre-mix is from about 15,000 cps to about 150,000 cps, the optional continuous heating should be utilized before the aeration step. In an additional preferred embodiment, additional heat is applied during the aeration process to try and maintain an elevated temperature during the aeration. This can be accomplished via conductive heating from one or more surfaces, injection of steam or other processing means.

Without being limited by a theory, the act of pre-heating the pre-mixture before the aeration step provides a means for lowering the viscosity of pre-mixtures comprising higher percent solids content for improved introduction of bubbles into the mixture and formation of the desired porous solid structure. Achieving higher percent solids content is desirable so as to reduce the energy requirements for drying. The increase of percent solids, and therefore conversely the decrease in water level content, and increase in viscosity is believed to affect the bubble drainage from the pre-mixture during the drying step. The drainage and evaporation of water from the pre-mixture during drying is believed to be critical to the formation of the desired predominantly open-celled porous solid structure described herein.

Pre-heating of the pre-mixture enables the manufacture of the desired fast dissolving porous solid structure from more viscous processing mixtures with higher percent solids levels that would normally produce slow dissolving and predominantly closed celled porous structures. While not being bound to theory, the increased temperature is believed to influence controlled bubble drainage from the thin film bubble facings into the plateau borders of the three dimensional foam generating openings between the bubbles (formation of open-cells) simultaneous to the solidification of the resulting plateau border structure (driven by evaporation). The demonstrated ability to achieve such inter-connected open-celled solid foam architectures with good mechanical integrity and visual appearance of the Article produced via the present invention and without collapse of the "unstable" foam structure during the drying process is surprising. The alternative predominantly closed celled porous solids that are typically produced without the processing innovations described herein have significantly poorer dissolution and do not meet the structural parameters encompassed by the porous solid structure described herein.

Moreover, the higher % solids and viscosity pre-mixtures resulted in solids with significantly less percent (%) shrinkage from the drying process while still resulting in porous solid structure with fast dissolution rates. On the one hand this is intuitive as the higher viscosities during the drying process should serve to mitigate the drainage and bubble rupture/collapse/coalescence that give rise to the shrinkage. However, on the other hand this is counterintuitive as such reduced drainage should mitigate the formation of the desired predominantly open-celled porous solid structure (with a minimum degree of cell interconnectivity) during the drying process.

Aeration of Pre-Mixture

The aeration of the pre-mixture is accomplished by introducing a gas into the pre-mixture, preferably by mechanical mixing energy but also may be achieved via chemical means to form an aerated mixture. The aeration may be accomplished by any suitable mechanical processing means, including but not limited to: (i) Batch tank aeration via mechanical mixing including planetary mixers or other suitable mixing vessels, (ii) semi-continuous or continuous aerators utilized in the food industry (pressurized and non-pressurized), or (iii) spray-drying the processing mixture in order to form aerated beads or particles that can be compressed such as in a mould with heat in order to form the porous solid.

Less preferred, but also envisioned in aeration with chemical foaming agents by in-situ gas formation (via chemical reaction of one or more ingredients, including formation of carbon dioxide ($CO_2$ (g)) by an effervescent system.

In a particular embodiment, it has been discovered that the Article can be prepared within continuous pressurized aerators that are conventionally utilized within the foods industry in the production of marshmallows. Suitable continuous pressurized aerators include the Morton whisk (Morton Machine Co., Motherwell, Scotland), the Oakes continuous automatic mixer (E.T. Oakes Corporation, Hauppauge, N.Y.), the Fedco Continuous Mixer (The Peerless Group, Sidney, Ohio), and the Preswhip (Hosokawa Micron Group, Osaka, Japan).

Forming the Aerated Wet Pre-Mixture

The forming of the aerated wet pre-mixture may be accomplished by any suitable means to form the mixture in a desired shape or shapes including, but not limited to (i) depositing the aerated mixture to specially designed moulds comprising a non-interacting and non-stick surface such as TEFLON®, metal, HDPE, polycarbonate, NEOPRENE®, rubber, LDPE, glass and the like; (ii) depositing the aerated mixture into cavities imprinted in dry granular starch contained in a shallow tray; and (iii) depositing the aerated mixture onto a continuous belt or screen comprising any non-interacting or non-stick material such as TEFLON®, metal, HDPE, polycarbonate, NEOPRENE®, rubber, LDPE, glass and the like, the resulting dried product may be later stamped, cut, embossed or stored on a roll. The formation results in a formed aerated wet pre-mixture.

The wet density range of the aerated pre-mixture ranges from about 0.15 g/cm$^3$ to about 0.50 g/cm$^3$, preferably from about 0.20 g/cm$^3$ to about 0.45 g/cm$^3$, more preferably from about 0.25 g/cm$^3$ to about 0.40 g/cm$^3$, and even more preferably from about 0.30 g/cm$^3$ to about 0.35 g/cm$^3$.

Drying the Formed Aerated Wet Pre-Mixture

The drying of the formed aerated wet pre-mixture may be accomplished by any suitable drying environment means including, but not limited to (i) drying room(s) including rooms with controlled temperature and pressure or atmospheric conditions; (ii) ovens including non-convection or convection ovens with controlled temperature and optionally humidity; (iii) Truck/Tray driers, (iv) multi-stage inline driers; (v) impingement ovens; (vi) rotary ovens/driers; (vii) inline roasters; (viii) rapid high heat transfer ovens and driers; (ix) dual plenum roasters, (x) conveyor driers, and (xi) vacuum drying chambers.

In one embodiment, the drying environment is selected from the group consisting of one or more drying rooms, convection ovens, Truck/Tray driers, multi-stage inline driers, impingement ovens/driers, rotary ovens/driers, inline roasters, rapid high heat transfer ovens and driers, dual plenum roasters, conveyor driers, vacuum drying chambers and combinations thereof, such that the drying environment is between 100° C. and 150° C.

Other suitable drying environments include "volumetric heating" techniques using high frequency electromagnetic fields such as Microwave Drying and Radio Frequency (RF) Drying. With these techniques, the energy is transferred electromagnetically through the aerated wet pre-mixture rather than by conduction or convection.

The drying environment is such that the formed aerated wet pre-mixture is dried to a dry density of from about 0.10 g/cm$^3$ to about 0.40 g/cm$^3$.

In one embodiment, the drying environment is heated to a temperature between 100° C. and 150° C. In one embodiment, the drying temperature is between 105° C. and 145° C. In another embodiment, the drying temperature is between 110° C. and 140° C. In a further embodiment, the drying temperature is between 115° C. and 135° C.

It has been found that increasing the surrounding air temperature of the drying step to about 100° C. to about 150° C. decreases the drying time of the formed aerated wet pre-mixture in forming the Article while maintaining the desired dissolution properties of the Article. It has been found that increasing surrounding air temperature levels from ambient temperature (25° C.) to 40° C. produced a suitable Article, but drying times to achieve a final moisture contents were several hours (typically requiring overnight drying). Increasing the surrounding air temperature of the drying step to 75° C. for a period of about 2 hours to the desired dry density provided an unsuitable Article and producing a denser bottom region including the formation of continuous sticky film on the bottom surface (adjacent to the mold) of the formed solid with poorer dissolution. While not being bound to theory, it is believed that this denser bottom region and formed continuous film serve as a rate limiting barrier for water ingress thereby adversely affecting the dissolution performance of the overall porous solid.

Surprisingly, it was found that an increase in the surrounding air temperature above 75° C. for the drying step to about 100° C. to about 150° C. provides acceptable properties for the Article within a 60 minute or less time frame while improving the desired dissolution properties. This is counter-intuitive given the poorer results observed upon increasing the temperature from 40° C. to 75° C. Moreover, this temperature range is above the boiling point of water and would thereby be expected to result in water vapour evaporation rates that likely exceed the rate of water vapour escape from the solid to the surrounding environment and resulting in the regional build-up of excessive internal solid pressure leading to increased expansion/thickness or "humped" cross sections of the resulting material. While not being bound to theory, it is believed that the initial aerated wet foam closed cells coalesce together during the critical stages of the drying process under these preferred temperature conditions, creating interconnected open-celled channels extending to the surface of the solid, and thereby enabling the facile escape of the water vapour molecules without excessive pressure build-up and ensuing regional expansion of the resulting solid.

Increases in the drying temperature beyond 150° C. were generally found by the Applicants to lead to regional solid expansion as well as partial discoloration of the solid surface which is indicative of chemical decomposition at these elevated temperatures.

In another embodiment, it has been found that Articles according to the present invention can be produced with a further improvement in the bottom region by Microwave drying. While not being bound to theory, it is believed that the internal heating afforded by Microwave heating technology helps to mitigate the drainage from the central region into the bottom region (adjacent to the mold surface) during the drying process and thereby creating a less dense bottom region and an overall structure with a more uniform density.

Importantly, microwave drying times of less than about 3 minutes result in undesired regional solid expansion of the Article. While not being bound to theory, this is believed to be due to water vapour evaporation rates that exceed the rate of water vapour escape from the solid as described herein above. To achieve drying times beyond 3 minutes, Microwave drying is preferably achieved via a low energy density applicator such as are available via Industrial Microwave Systems L.L.C (Morrisville, N.C. http://www.industrialmicrowave.com/). In particular, a low energy two wide wave applicators in series microwave applicator system is preferred with two or more low energy applicator regions (about 5 kW). Ideally, the air environment within the low energy microwave applicator system is at an elevated temperature (typically from about 35° C. to about 90° C. and preferably from about 40° C. to about 70° C. and with good circulation so as to facilitate the removal of the resulting humidity.

In one embodiment, the drying time to the desired dry density is from about 3 minutes to about 90 minutes, in another embodiment from about 5 minutes to about 60 minutes, in another embodiment from about 7 minutes to about 45 minutes. The drying step results in the Article. Drying times of less than about 3 minutes result in undesired regional solid cross-sectional expansion of the resulting Article, whereas drying times beyond these values and up to 2 to 3 hours result in excessive densification of the bottom surface of the Article leading to poorer dissolution. Drying times between 3 hours and 20 hours (overnight) lead to acceptable Articles, but suffer from poorer economics of production.

The drying times that can be achieved via convective drying are between about 10 minutes to about 90 minutes, in another embodiment from about 20 minutes to about 60 minutes, and in another embodiment from about 30 minutes to about 45 minutes.

The drying times that can be achieved via Microwave drying are between about 3 minutes and about 25 minutes, in another embodiment between about 5 minutes and about 20 minutes, and in another embodiment between about 7 minutes and about 15 minutes.

The resulting Article (dried) may comprise a dry density of from about 0.10 g/cm$^3$ to about 0.40 g/cm$^3$, in one embodiment from about 0.11 g/cm$^3$ to about 0.30 g/cm$^3$, in another embodiment from about 0.12 g/cm$^3$ to about 0.25 g/cm$^3$, and in another embodiment from about 0.13 g/cm$^3$ to about 0.20 g/cm$^3$.

Further Optional Steps

Further optional steps not recited above may be added at any point during or after the recited process. Optional ingredients may be imparted during any of the above described four processing steps or even after the drying process. Further optional steps may include further finishing steps, such as the addition of heat sensitive materials including but not limited to perfumes and enzymes; cutting of the Article into a smaller size; puncturing or slitting the Article, further manipulation of the Article such a forming a three-dimensional shape, printing, texturizing, mixing the Article into another composition, laminating the Article with another material, packaging the Article and other process steps.

Additional steps that can be used in the present process include cutting the resulting Article into smaller sizes, puncturing the Article with needles or slitting the Article. The size of the Article will depend upon the desired dosage amount of actives, or in this case surfactant. The frequency of perforation or slitting is confined to maintain the structural integrity of the Article such that it can still be handled.

The Article may be further manipulated into a shape or form other than a flat plane or sheet. Other three-dimensional shapes may include spherical bead or ball, flowers, flower petals, berry shapes and various known pasta shapes. As such the process may further include a step whereby the Article is manipulated into a three-dimensional shape.

The Article may undergo different manipulation such as being printed upon or texturized by dimpled, waffled or otherwise topographically patterned surfaces including letters, logos or figures. The printing or texturizing of the Article can also be the result of creping processes, imprinted coatings, embossing patterns, laminating to other layers having raised portions, or the result of the physical form of the dissolvable porous solid substrate itself. The printing step may include printing by spraying, knife, rod, kiss, slot, painting, printing such as flexographic (flexo) printing and combinations thereof. Therefore, the present process can further include the step of printing or texturing the Article.

The Article may be utilized by being mixed with other compositions or products. The mixing should not detract from the dissolution properties herein described. Therefore the present process may further comprise the step of mixing the Article with another composition, mixing the Article with another product.

The Article may be packaged for consumption individually or in a plurality of Articles. The Article may be included in a kit wherein various types of products are supplied, including Articles with different compositions, Article(s) with other products making up a regime of series of products for a desired benefit, or Article(s) with other products unrelated such as a toiletry travel kit for travel on airplanes.

Suitable packaging material may be selected such that the Article is protected from inadvertent exposure to liquids. The packaging material may be air and/or vapor permeable, dependent upon the environment in which the Article is to be sold.

The process may further include a step of packaging the Article individually for sale as a product. The process may further include a step of packaging a plurality of Article for sale as a product. The process may further include a step of including a packaged Article in a kit for sale as a product. The packaging step is undertaken after the formation of the Article, preferably after the Article is cut into a suitable size. The Article may be packaged on the same line as the production of Article or the Article may be collected, shipped or stored, and then packaged at a later time.

Percent (%) Solids in Pre-Mixture

The processing mixtures of the present invention comprise: from about 15% to about 70% solids, in one embodiment from about 30% to about 70% solids, in one embodiment from about 30% to about 60% solids, in one embodiment from about 32% to about 55% solids, in one embodiment from about 34% to about 50%, and in another embodiment from about 36% to about 45% solids, by weight of the pre-mixture before drying. The % solids content is the summation of the weight percentages by weight of the total processing mixture of all of the solid, semi-solid and liquid components excluding water and any obviously volatile materials such as low boiling alcohols.

Viscosity of Pre-Mixture

At ambient temperature and pressure, the processing mixtures of the present invention have a viscosity of from about 2,500 cps to about 150,000 cps, in one embodiment from about 15,000 cps to about 150,000 cps, in one embodiment from about 20,000 cps to about 125,000 cps, in another embodiment from about from about 25,000 cps to about 100,000 cps, and in still another embodiment from about 30,000 cps to about 75,000 cps. The processing mixture viscosity values are measured using a TA Instruments AR500 Rheometer with 4.0 cm diameter parallel plate and 1,200 micron gap at a shear rate of 1.0 reciprocal seconds for a period of 30 seconds at 23° C.

Surfactants

The Article comprises one or more surfactants suitable for application to the hair or skin. Surfactants suitable for use in the Article include anionic surfactants, nonionic surfactants, cationic surfactants, zwitterionic surfactants, amphoteric surfactants, polymeric surfactants or combinations thereof.

In one embodiment, the Article is a lathering dissolvable solid personal care product (dried) and comprises from about 23% to about 75% by weight of the Article of surfactant, in one embodiment from about 30% to about 70% by weight of the Article of surfactant, in one embodiment from about 40% to about 65% by weight of the Article of surfactant. In such cases, the pre-mixture may comprise from about 8% to about 30% by weight of the pre-mixture of surfactant, in one embodiment from about 13% to about 28% by weight of the pre-mixture of surfactant, in one embodiment from about 18% to about 25% by weight of the pre-mixture of surfactant.

Non-limiting examples of anionic surfactants suitable for use herein include alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, sodium lauroyl glutamate, and combinations thereof.

Preferred anionic surfactants for use in the personal care compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

Amphoteric surfactants suitable for use herein include, but are not limited to derivatives of aliphatic secondary and tertiary amines in which the aliphatic radical can be straight or branched chain and wherein one substituent of the aliphatic substituents contains from about 8 to about 18 carbon atoms and one contains an anionic water solubilizing group, e.g., carboxy, sulfonate, sulfate, phosphate, or phosphonate. Examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378, and mixtures thereof. The family of amphoacetates derived from the reaction of sodium chloroacetate with amidoamines to produce alkanoyl amphoacetates are particularly effective, e.g. lauryolamphoacetate, and the like.

Zwitterionic surfactants suitable for use herein include, but are not limited to derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Other zwitterionic surfactants suitable for use herein include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, lauryl bis-(2-hydroxypropyl)alpha-carboxyethyl betaine, and mixtures thereof. The sulfobetaines may include coco dimethyl sulfopropyl betaine, stearyl dimethyl sulfopropyl betaine, lauryl dimethyl sulfoethyl betaine, lauryl bis-(2-hydroxyethyl)sulfopropyl betaine and mixtures thereof. Also suitable amphoteric surfactants include amidobetaines and amidosulfobetaines, wherein the RCONH(CH$_2$)$_3$ radical is attached to the nitrogen atom of the betaine are also useful herein.

Cationic surfactants may include a DEQA compound. The DEQA compounds encompass a description of diamido actives as well as actives with mixed amido and ester linkages.

Preferred DEQA compounds are typically made by reacting alkanolamines such as MDEA (methyldiethanolamine) and TEA (triethanolamine) with fatty acids. Some materials that typically result from such reactions include N,N-di(acyloxyethyl)-N,N-dimethylammonium chloride or N,N-di(acyloxyethyl)-N,N-methylhydroxyethylammonium methylsulfate wherein the acyl group is derived from animal fats, unsaturated, and polyunsaturated, fatty acids (See U.S. Pat. No. 5,759,990 at column 4, lines 45-66). Additional non-limiting examples of such DEQA compounds are described in U.S. Pat. No. 5,580,481 and U.S. Pat. No. 5,476,597.

Other suitable actives for use as a cationic surfactant include reaction products of fatty acids with dialkylenetriamines in, e.g., a molecular ratio of about 2:1, said reaction products containing compounds of the formula:

$$R^1-C(O)-NH-R^2-NH-R^3-NH-C(O)-R^1$$

wherein $R^1$, $R^2$ are defined as above, and each $R^3$ is a $C_{1-6}$ alkylene group, preferably an ethylene group. Examples of these actives are reaction products of tallow acid, canola acid, or oleic acids with diethylenetriamine in a molecular ratio of about 2:1, said reaction product mixture containing N,N"-ditallowoyldiethylenetriamine, N,N"-dicanola-oyldiethylenetriamine, or N,N"-dioleoyldiethylenetriamine, respectively, with the formula:

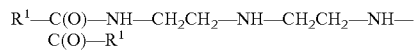

$$R^1-C(O)-NH-CH_2CH_2-NH-CH_2CH_2-NH-C(O)-R^1$$

wherein $R^2$ and $R^3$ are divalent ethylene groups, $R^1$ is defined above and an acceptable examples of this structure when $R^1$ is the oleoyl group of a commercially available oleic acid derived from a vegetable or animal source, include EMERSOL® 223LL or EMERSOL® 7021, available from Henkel Corporation.

Another active for use as a cationic surfactant has the formula:

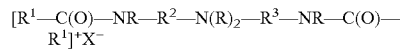

$$[R^1-C(O)-NR-R^2-N(R)_2-R^3-NR-C(O)-R^1]^+X^-$$

wherein R, $R^1$, $R^2$, $R^3$ and $X^-$ are defined as above. Examples of this active are the di-fatty amidoamines based softener having the formula:

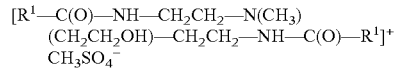

$$[R^1-C(O)-NH-CH_2CH_2-N(CH_3)(CH_2CH_2OH)-CH_2CH_2-NH-C(O)-R^1]^+ CH_3SO_4^-$$

wherein $R^1$—C(O) is an oleoyl group, soft tallow group, or a hardened tallow group available commercially from Degussa under the trade names VARISOFT® 222LT, VARISOFT® 222, and VARISOFT® 110, respectively.

A second type of DEQA ("DEQA (2)") compound suitable as a active for use as a cationic surfactant has the general formula:

$$[R_3N^+CH_2CH(YR^1)(CH_2YR^1)]X^-$$

wherein each Y, R, $R^1$, and $X^-$ have the same meanings as before.

These types of agents and general methods of making them are disclosed in U.S. Pat. No. 4,137,180, Naik et al., issued Jan. 30, 1979. An example of a preferred DEQA (2) is the "propyl" ester quaternary ammonium fabric softener active having the formula 1,2-di(acyloxy)-3-trimethylammoniopropane chloride.

In another embodiment, the Article is a substantially non-lathering dissolvable solid personal care product and comprises from about 0% to about 10% by weight of the Article of an ionic (anionic, zwitterionic, cationic and mixtures thereof) surfactant, in one embodiment from about 0% to about 5% by weight of the Article of an ionic surfactant, and in one embodiment from about 0% to about 2.5% by weight of the Article of an ionic surfactant, and from about 1% to about 50% by weight of the Article of a nonionic or polymeric surfactant, in one embodiment from about 5% to about 45% by weight of the Article of a nonionic or polymeric surfactant, and in one embodiment from about 10% to about 40% by weight of the Article of a nonionic or polymeric surfactant, and combinations thereof.

Suitable nonionic surfactants for use in the present invention include those described in McCutcheion's Detergents and Emulsifiers, North American edition (1986), Allured Publishing Corp., and McCutcheion's Functional Materials, North American edition (1992). Suitable nonionic surfactants for use in the personal care compositions of the present invention include, but are not limited to, polyoxyethylenated alkyl phenols, polyoxyethylenated alcohols, polyoxyethylenated polyoxypropylene glycols, glyceryl esters of alkanoic acids, polyglyceryl esters of alkanoic acids, propylene glycol esters of alkanoic acids, sorbitol esters of alkanoic acids, polyoxyethylenated sorbitor esters of alkanoic acids, polyoxyethylene glycol esters of alkanoic acids, polyoxyethylenated alkanoic acids, alkanolamides, N-alkylpyrrolidones, alkyl glycosides, alkyl polyglucosides, alkylamine oxides, and polyoxyethylenated silicones.

In a highly preferred embodiment, the nonionic surfactant selected from sorbitan esters and alkoxylated derivatives of sorbitan esters including sorbitan monolaurate (SPAN® 20), sorbitan monopalmitate (SPAN® 40), sorbitan monostearate (SPAN® 60), sorbitan tristearate (SPAN® 65), sorbitan monooleate (SPAN® 80), sorbitan trioleate (SPAN® 85), sorbitan isostearate, polyoxyethylene (20) sorbitan monolaurate (Tween® 20), polyoxyethylene (20) sorbitan monopalmitate (Tween® 40), polyoxyethylene (20) sorbitan monostearate (Tween® 60), polyoxyethylene (20) sorbitan monooleate (Tween® 80), polyoxyethylene (4) sorbitan monolaurate (Tween® 21), polyoxyethylene (4) sorbitan monostearate (Tween® 61), polyoxyethylene (5) sorbitan monooleate (Tween® 81), all available from Uniqema, and combinations thereof.

Suitable polymeric surfactants for use in the personal care compositions of the present invention include, but are not limited to, block copolymers of ethylene oxide and fatty alkyl residues, block copolymers of ethylene oxide and propylene oxide, hydrophobically modified polyacrylates, hydrophobically modified celluloses, silicone polyethers, silicone copolyol esters, diquaternary polydimethylsiloxanes, and co-modified amino/polyether silicones.

Polymer

The one or more water-soluble polymers suitable for the Article herein are selected such that their weighted average molecular weight is from about 40,000 to about 500,000, in one embodiment from about 50,000 to about 400,000, in yet another embodiment from about 60,000 to about 300,000, and in still another embodiment from about 70,000 to about 200,000. The weighted average molecular weight is computed by summing the average molecular weights of each polymer raw material multiplied by their respective relative weight percentages by weight of the total weight of polymers present within the porous solid.

The water-soluble polymer(s) of the Article can include, but are not limited to, synthetic polymers including polyvinyl alcohols, polyvinylpyrrolidones, polyalkylene oxides, polyacrylates, caprolactams, polymethacrylates, polymethylmethacrylates, polyacrylamides, polymethylacrylamides, polydimethylacrylamides, polyethylene glycol monomethacrylates, copolymers of acrylic acid and methyl acrylate, polyurethanes, polycarboxylic acids, polyvinyl acetates, polyesters, polyamides, polyamines, polyethyleneimines, maleic/(acrylate or methacrylate) copolymers, copolymers of methylvinyl ether and of maleic anhydride, copolymers of vinyl acetate and crotonic acid, copolymers of vinylpyrrolidone and of vinyl acetate, copolymers of vinylpyrrolidone and of caprolactam, vinyl pyrollidone/vinyl acetate copolymers, copolymers of anionic, cationic and amphoteric monomers, and combinations thereof.

The water-soluble polymer(s) of the Article may also be selected from naturally sourced polymers including those of plant origin examples of which include karaya gum, tragacanth gum, gum Arabic, acemannan, konjac mannan, acacia gum, gum ghatti, whey protein isolate, and soy protein isolate; seed extracts including guar gum, locust bean gum, quince seed, and psyllium seed; seaweed extracts such as Carrageenan, alginates, and agar; fruit extracts (pectins); those of microbial origin including xanthan gum, gellan gum, pullulan, hyaluronic acid, chondroitin sulfate, and dextran; and those of animal origin including casein, gelatin, keratin, keratin hydrolysates, sulfonic keratins, albumin, collagen, glutelin, glucagons, gluten, zein, and shellac.

Modified natural polymers are also useful as water-soluble polymer(s) in the Article. Suitable modified natural polymers include, but are not limited to, cellulose derivatives such as hydroxypropylmethylcellulose, hydroxymethylcellulose, hydroxyethylcellulose, methylcellulose, hydroxypropylcellulose, ethylcellulose, carboxymethylcellulose, cellulose acetate phthalate, nitrocellulose and other cellulose ethers/esters; and guar derivatives such as hydroxypropyl guar.

Preferred water-soluble polymers of the Article include polyvinyl alcohols, polyvinylpyrrolidones, polyalkylene oxides, starch and starch derivatives, pullulan, gelatin, hydroxypropylmethylcelluloses, methycelluloses, and carboxymethycelluloses.

More preferred water-soluble polymers of the Article include polyvinyl alcohols, and hydroxypropylmethylcelluloses. Suitable polyvinyl alcohols include those available from Celanese Corporation (Dallas, Tex.) under the CELVOL trade name including, but not limited to, CELVOL 523, CELVOL 530, CELVOL 540, CELVOL 518, CELVOL 513, CELVOL 508, CELVOL 504, and combinations thereof. Suitable hydroxypropylmethylcelluloses include those available from the Dow Chemical Company (Midland, Mich.) under the METHOCEL trade name including, but not limited, to METHOCEL E50, METHOCEL E15, METHOCEL E6, METHOCEL ES, METHOCEL E3, METHOCEL F50, METHOCEL K100, METHOCEL K3, METHOCEL A400, and combinations thereof including combinations with above mentioned hydroxypropylmethylcelluloses.

The Article (dried) may comprise from about 10% to about 50% by weight of the Article of water soluble polymer, in one embodiment from about 15% to about 40% by weight of the Article of water soluble polymer, in one embodiment from about 20% to about 30% by weight of the Article of water soluble polymer.

The pre-mixture may comprise from about 3% to about 20% by weight of the pre-mixture of water soluble polymer, in one embodiment from about 5% to about 15% by weight of the pre-mixture of water soluble polymer, in one embodiment from about 7% to about 10% by weight of the pre-mixture of water soluble polymer.

Plasticizer

The Article may comprise a water soluble plasticizing agent suitable for use in compositions discussed herein. Non-limiting examples of suitable plasticizing agents include polyols, copolyols, polycarboxylic acids, polyesters and dimethicone copolyols.

Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol and other mono- and polyhydric low molecular weight alcohols (e.g., $C_2$-$C_8$ alcohols); mono di- and oligo-saccharides such as fructose, glucose, sucrose, maltose, lactose, and high fructose corn syrup solids and ascorbic acid.

Examples of polycarboxylic acids include, but are not limited to citric acid, maleic acid, succinic acid, polyacrylic acid, and polymaleic acid.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate.

Examples of suitable dimethicone copolyols include, but are not limited to, PEG-12 dimethicone, PEG/PPG-18/18 dimethicone, and PPG-12 dimethicone.

Other suitable platicizers include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of $C_2$-$C_{10}$ alcohols and acids); and any other water soluble plasticizer known to one skilled in the art of the foods and plastics industries; and mixtures thereof.

Preferred placticizers include glycerin and propylene glycol. EP 0283165 B1 discloses other suitable plasticizers, including glycerol derivatives such as propoxylated glycerol.

The pre-mixture may comprise from about 0.3% to about 8% by weight of the pre-mixture of plasticizer, in one embodiment from about 1% to about 5% by weight of the pre-mixture of plasticizer, in one embodiment from about 2% to about 4% by weight of the pre-mixture of plasticizer.

The Article (dried) may comprise from about 1% to about 25% by weight of the Article of plasticizer, in one embodiment from about 3% to about 20% by weight of the Article of plasticizer, in one embodiment from about 5% to about 15% by weight of the Article of plasticizer.

Optional Ingredients

The Article may further comprise other optional ingredients that are known for use or otherwise useful in compositions, provided that such optional materials are compatible with the selected essential materials described herein, or do not otherwise unduly impair product performance.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992.

Emulsifiers suitable as an optional ingredient herein include mono- and di-glycerides, fatty alcohols, polyglycerol esters, propylene glycol esters, sorbitan esters and other emulsifiers known or otherwise commonly used to stabilized air interfaces, as for example those used during preparation of aerated foodstuffs such as cakes and other baked goods and confectionary products, or the stabilization of cosmetics such as hair mousses.

Further non-limiting examples of such optional ingredients include preservatives, perfumes or fragrances, coloring agents or dyes, conditioning agents, hair bleaching agents, thickeners, moisturizers, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, anti-dandruff agents, perfumes, exfoliating agents, acids, bases, humectants, enzymes, suspending agents, pH modifiers, hair colorants, hair perming agents, pigment particles, anti-acne agents, anti-microbial agents, sunscreens, tanning agents, exfoliation particles, hair growth or restorer agents, insect repellents, shaving lotion agents, co-solvents or other additional solvents, and similar other materials.

Suitable conditioning agents include high melting point fatty compounds, silicone conditioning agents and cationic conditioning polymers. Suitable materials are discussed in US 2008/0019935, US 2008/0242584 and US 2006/0217288.

Non-limiting examples of product type embodiments for use by the Article include hand cleansing substrates, hair shampoo or other hair treatment substrates, body cleansing substrates, shaving preparation substrates, fabric care substrate (softening), dish cleaning substrates, pet care substrates, personal care substrates containing pharmaceutical or other skin care active, moisturizing substrates, sunscreen substrates, chronic skin benefit agent substrates (e.g., vitamin-containing substrates, alpha-hydroxy acid-containing substrates, etc.), deodorizing substrates, fragrance-containing substrates, and so forth.

Distance to Maximum Force Method: Measured via a Rupture Method on a Texture Analyzer using a TA-57R cylindrical probe with Texture Exponent 32 Software. The Article should have a thickness of between 4 to 7 mm and cut in a circle with a diameter of at least 7 mm for this method; or carefully cut or stacked to be within this overall thickness and diameter range. The porous solid sample is carefully mounted on top of the cylinder with four screws mounted on top with the top lid affixed in place on top of the sample. There is a hole in the center of the cylinder and its lid which allows the probe to pass through and stretch the sample. The sample is measured with a pre-test speed of 1 mm per second, a test speed of 2 mm per second and a post test speed of 3 mm per second over a total distance of 30 mm. The distance to maximum force is recorded.

Hand Dissolution Method: One Article, with dimensions of approximately 43 mm×43 mm×4-6 mm, is placed in the palm of the hand while wearing nitrile gloves. 7.5 $cm^3$ of from about 30° C. to about 35° C. tap water is quickly applied to the product via syringe. Using a circular motion, palms of hands are rubbed together 2 strokes at a time until dissolution occurs (up to 30 strokes). The hand dissolution value is reported as the number of strokes it takes for complete dissolution or as 30 strokes as the maximum.

Lather Profile: Lather Volume

The Article provides a lather profile as described hereafter. The lather volume assessment is performed on 15 g/10 inch flat Oriental virgin hair switches that have been treated with 0.098 g of artificial liquid sebum [10-22% olive oil, 18-20% coconut oil, 18-20% oleic acid, 5-9% lanolin, 5-9% squalene, 3-6% palmitic acid, 3-6% paraffin oil, 3-6% dodecane, 1-4% stearic acid, 1-4% cholesterol, 1-4% coconut fatty acid, 18-20% choleth-24]. The hair switch is rinsed with 9-11 grain, 100° F. water at 1.5 gallons/min for 20 seconds with a shower nozzle. For testing the liquid control products, 0.75 $cm^3$ of liquid product are applied to the center of the switch, the lower portion of hair on the switch is then rubbed over the product on the hair 10 times in a circular motion, followed by 40 strokes back and forth (a total of 80 strokes). Lather speed is recorded as the number of strokes when the first lather is obviously generated during the 80 strokes. Lather from operator's gloves is transferred to a graduated cylinder with a 3.5 cm inside diameter and with total capacities of either 70 ml, 110 ml, or 140 ml depending on the total amount of lather generated (height modification of standard sized graduated cylinders via a glass shop). Lather from hair is gathered using one downward stroke on the switch with a tight grip and is also placed into the cylinder. Total lather volume is recorded in milliliters. Three runs per test sample are performed and the mean of the three values is calculated. When testing the Article, 0.20+/−0.01 grams of product are weighed with the aid of scissors if required and applied to the switch and then 2 $cm^3$ of additional water are added to the product via syringe. The lathering technique is then performed as described for liquid products after a 10 second waiting time.

As used herein, the terms "substantially non-lathering" and "non-lathering" are used to mean a lather volume of from 0 ml to 20 ml.

% Shrinkage

The % shrinkage is computed by subtracting the final measured thickness from the original formed thickness prior to the drying step and dividing by the formed thickness and multiplying by 100 to generate a percentage shrinkage. The latter original formed thickness can be approximated by the depth of the mold in instances where the wet pre-mixture is applied level to the top of the mold as described herein.

The Article has a maximum Cell Wall Thickness. The Article has a Cell Wall Thickness of from about from about 0.02 mm to about 0.15 mm, in one embodiment from about 0.025 mm to about 0.12 mm, in another embodiment from about 0.03 mm to about 0.09 mm, and in still another embodiment from about 0.035 mm to about 0.06 mm.

The Cell Wall Thickness is computed from the scanned images via a micro computed tomography system (μCT80, SN 06071200, Scanco Medical AG) as described herein. The Cell Wall Thickness is determined according to the method defined for the measurement of Trabecular Thickness using Scanco Medical's Bone Trabecular Morphometry evaluation. The definition of Trabecular Thickness as taken from the Scanco User's manual: Trabecular Thickness uses a Euclidean distance transformation (EDM), which calculates the Euclidean distance from any point in the foreground to the nearest background point. The Trabecular Thickness measure represents twice the centerline values associated with the local maxima of the EDM, which represents the distance to the center of the object (twice this distance will yield the thickness).

The Article also has a minimum Specific Surface Area. The Article has a Specific Surface Area of from about 0.03 $m^2/g$ to about 0.25 $m^2/g$, in one embodiment from about 0.035 $m^2/g$ to about 0.22 $m^2/g$, in another embodiment from about 0.04 $m^2/g$ to about 0.19 $m^2/g$, and in still another embodiment from about 0.045 $m^2/g$ to about 0.16 $m^2/g$.

The Specific Surface Area is measured via a gas adsorption technique. Surface Area is a measure of the exposed surface of a solid sample on the molecular scale. The BET (Brunauer, Emmet, and Teller) theory is the most popular model used to determine the surface area and is based upon gas adsorption isotherms. Gas Adsorption uses physical adsorption and capillary condensation to measure a gas adsorption isotherm. The technique is summarized by the following steps; a sample is placed in a sample tube and is heated under vacuum or flowing gas to remove contamination on the surface of the sample. The sample weight is obtained by subtracting the empty sample tube weight from the combined weight of the degassed sample and the sample tube. The sample tube is then placed on the analysis port and the analysis is started. The first step in the analysis process is to evacuate the sample tube, followed by a measurement of the free space volume in the sample tube using helium gas at liquid nitrogen temperatures. The sample is then evacuated a second time to remove the helium gas. The instrument then begins collecting the adsorption isotherm by dosing krypton gas at user specified intervals until the requested pressure measurements are achieved. Samples may then analyzed using an ASAP 2420 with krypton gas adsorption. It is recommended that these measurements be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in a book, "Analytical Methods in Fine particle Technology", by Clyde On and Paul Webb.

The Article is preferably a flat, flexible substrate in the form of a pad, a strip or tape and having a thickness of from about 0.5 mm to about 10 mm, in one embodiment from about 1 mm to about 9 mm, in another embodiment from about 2 mm to about 8 mm, and in a further embodiment from about 3 mm to about 7 mm as measured by the below methodology. In the case of cylindrical, spherical, or other objects with more of a third dimension versus a pad or strip, the thickness is taken as the maximum distance of the shortest dimension, i.e., the diameter of a sphere or cylinder for instance, and the thickness ranges are the same as described above.

The thickness of the dissolvable porous solid (i.e., substrate or sample substrate) is obtained using a micrometer or thickness gage, such as the Mitutoyo Corporation Digital Disk Stand Micrometer Model Number IDS-1012E (Mitutoyo Corporation, 965 Corporate Blvd, Aurora, Ill., USA 60504). The micrometer has a 1 inch diameter platen weighing about 32 grams, which measures thickness at an application pressure of about 40.7 psi (6.32 $gm/cm^2$).

The thickness of the dissolvable porous solid is measured by raising the platen, placing a section of the sample substrate on the stand beneath the platen, carefully lowering the platen to contact the sample substrate, releasing the platen, and measuring the thickness of the sample substrate in millimeters on the digital readout. The sample substrate should be fully extended to all edges of the platen to make sure thickness is measured at the lowest possible surface pressure, except for the case of more rigid substrates which are not flat. For more rigid substrates which are not completely flat, a flat edge of the substrate is measured using only one portion of the platen impinging on the flat portion of the substrate.

The Article has a basis weight of from about 400 $grams/m^2$ to about 3,000 $grams/m^2$, in one embodiment from about 500 $grams/m^2$ to about 2,500 $grams/m^2$, in another embodiment from about 600 $grams/m^2$ to about 2,000 $grams/m^2$, and in still another embodiment from about 700 $grams/m^2$ to about 1,500 $grams/m^2$.

The Basis Weight of the dissolvable porous solid component of the personal care composition herein is calculated as the weight of the dissolvable porous solid component per area of the selected dissolvable porous solid ($grams/m^2$). The area is calculated as the projected area onto a flat surface perpendicular to the outer edges of the porous solid. For a flat object, the area is thus computed based on the area enclosed within the outer perimeter of the sample. For a spherical object, the area is thus computed based on the average diameter as 3.14×$(diameter/2)^2$. For a cylindrical object, the area is thus computed based on the average diameter and average length as diameter×length. For an irregularly shaped three dimensional object, the area is computed based on the side with the largest outer dimensions projected onto a flat surface oriented perpendicularly to this side. This can be accomplished by carefully tracing the outer dimensions of the object onto a piece of graph paper with a pencil and then computing the area by approximate counting of the squares and multiplying by the known area of the squares or by taking a picture of the traced area (preferably shaded-in for contrast) including a scale and using image analysis techniques.

The Article has a dry density of from about 0.08 g/cm$^3$ to about 0.30 g/cm$^3$, in one embodiment from about 0.10 g/cm$^3$ to about 0.25 g/cm$^3$, and in another embodiment from about 0.12 g/cm$^3$ to about 0.20 g/cm$^3$.

The dry density of the dissolvable porous solid is determined by the equation: Calculated Density=Basis Weight of porous solid/(Porous Solid Thickness×1,000). The Basis Weight and Thickness of the dissolvable porous solid are determined in accordance with the methodologies described herein.

Scanning Electron Microscope (SEM) Imaging:

Representative sections were cut from the sponge with a clean razor blade and mounted with the cut face up on a standard cryo-SEM stub. Samples were secured onto the stub with carbon tape and silver paint. Samples were imaged using an Hitachi S-4700 FE-SEM fitted with a Gatan Alto 2500 cryo stage. Samples were cooled to −95 dC before imaging in the microscope. Samples were lightly coated with Platinum to reduce charging. Representative images were collected at 2 kV, 20 uA extraction voltage, ultra high resolution mode using the lower secondary electron detector. Long working distances were used to allow the entire sample to be imaged in one frame.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

Examples 1-12

Surfactant/Polymer Liquid Processing Compositions

The following surfactant/polymer liquid processing compositions are prepared at the indicated weight percentages as described below. The liquid formulations differ on the ratio of anionic:amphoteric surfactant, the type of amphoteric surfactant, and the type of anionic surfactants:

TABLE 1

| Component | Ex. 1 | Ex. 2 | Ex. 3 |
| --- | --- | --- | --- |
| Weight Percent Solids | 28.1% | 28.9% | 29.5% |
| Anionic:Amphoteric (Zwitterionic) Ratio | 100:0 | 80:20 | 60:40 |
| Glycerin | 3.0 | 3.0 | 3.0 |
| Polyvinyl alcohol[1] | 7.4 | 7.4 | 7.4 |
| Sodium Lauroamphoacetate (26% activity)[2] | 0.0 | 14.6 | 29.2 |
| Ammonium Laureth-3 sulfate (25% activity) | 7.5 | 6.0 | 4.5 |
| Ammonium Undecyl sulfate (24% activity) | 30.3 | 24.3 | 18.2 |
| Ammonium Laureth-1 sulfate (70% activity) | 12.1 | 9.7 | 7.2 |
| Citric Acid | 0.04 | 0.6 | 1.0 |
| Distilled water | 39.7 | 34.4 | 29.5 |
| Total | 100.0 | 100.0 | 100.0 |
| pH | 6.1 | 6.4 | 6.1 |
| Viscosity (cp) | 5,300 | 8,200 | 14,500 |

[1]Sigma-Aldrich Catalog No. 363081, MW 85,000-124,000, 87-89% hydrolyzed
[2]McIntyre Group Ltd, University Park, IL, Mackam HPL-28ULS

TABLE 2

| Component | Ex. 4 | Ex. 5 | Ex. 6 |
| --- | --- | --- | --- |
| Weight Percent Solids | 33.0% | 36.0% | 39.0% |
| Anionic:Amphoteric (Zwitterionic) Ratio | 60:40 | 60:40 | 60:40 |
| Glycerin | 3.35 | 3.66 | 3.96 |
| Polyvinyl alcohol[1] | 8.27 | 9.02 | 9.77 |
| Sodium Lauroamphoacetate (26% activity)[2] | 32.64 | 35.60 | 38.57 |
| Ammonium Laureth-3 sulfate (25% activity) | 5.03 | 5.49 | 5.94 |
| Ammonium Undecyl sulfate (24% activity) | 20.34 | 22.19 | 24.04 |
| Ammonium Laureth-1 sulfate (70% activity) | 8.05 | 8.78 | 9.51 |
| Citric Acid | 1.12 | 1.22 | 1.32 |
| Distilled water | 21.20 | 14.04 | 6.88 |
| Total | 100.0 | 100.0 | 100.0 |
| pH | 6.6 | 6.7 | 6.7 |
| Viscosity (cp) | 23,900 | 37,600 | 50,900 |

[1]Sigma-Aldrich Catalog No. 363081, MW 85,000-124,000, 87-89% hydrolyzed
[2]McIntyre Group Ltd, University Park, IL, Mackam HPL-28ULS

TABLE 3

| Component | Ex. 7 | Ex. 8 | Ex. 9 | Ex. 10 |
| --- | --- | --- | --- | --- |
| Weight Percent Solids | 30.1% | 33.3% | 35.2% | 37.2% |
| Anionic:Amphoteric (Zwitterionic) Ratio | 60:40 | 60:40 | 60:40 | 60:40 |
| Glycerin | 3.0 | 3.2 | 3.4 | 3.6 |
| Polyvinyl alcohol[1] | 7.4 | 8.1 | 8.6 | 9.0 |
| Sodium Lauroamphoacetate (26% activity)[2] | 29.2 | 31.8 | 33.7 | 35.6 |
| Ammonium Laureth-3 sulfate (25% activity) | 4.5 | 4.9 | 5.2 | 5.5 |
| Ammonium Undecyl sulfate (24% activity) | 18.2 | 19.9 | 21.1 | 22.2 |
| Ammonium Laureth-1 sulfate (70% activity) | 7.3 | 8.0 | 8.4 | 8.9 |
| Cationic guar polymer[3] | 0.50 | 0.50 | 0.53 | 0.56 |
| Citric Acid | 0.95 | 1.6 | 1.7 | 1.8 |
| Distilled water | 28.95 | 22.0 | 17.4 | 12.8 |
| Total | 100.0 | 100.0 | 100.0 | 100.0 |
| pH | 6.4 | 5.7 | 5.5 | 5.4 |
| Viscosity (cp) | 19,200 | 32,200 | 52,400 | 64,900 |

[1]Sigma-Aldrich Catalog No. 363081, MW 85,000-124,000, 87-89% hydrolyzed
[2]McIntyre Group Ltd, University Park, IL, Mackam HPL-28ULS
[3]Jaguar C-500, available from Rhodia Inc. (Cranbury, New Jersey)

TABLE 4

| Component | Ex. 11 | Ex. 12 |
| --- | --- | --- |
| Weight Percent Solids | 30.1% | 33.3% |
| Anionic:Amphoteric (Zwitterionic) Ratio | 60:40 | 60:40 |
| Glycerin | 3.0 | 3.2 |
| Polyvinyl alcohol[1] | 7.4 | 8.1 |

TABLE 4-continued

| Component | Ex. 11 | Ex. 12 |
|---|---|---|
| Sodium Lauroamphoacetate (26% activity)[2] | 29.2 | 31.8 |
| Ammonium Laureth-3 sulfate (25% activity) | 4.5 | 4.9 |
| Ammonium Undecyl sulfate (24% activity) | 18.2 | 19.9 |
| Ammonium Laureth-1 sulfate (70% activity) | 7.3 | 8.0 |
| Cationic cellulose[3] | 0.50 | 0.5 |
| Citric Acid | 0.95 | 1.6 |
| Distilled water | 28.95 | 22.0 |
| Total | 100.0 | 100.0 |
| pH | 6.1 | 5.8 |
| Viscosity (cp) | 19,600 | 35,400 |

[1]Sigma-Aldrich Catalog No. 363081, MW 85,000-124,000, 87-89% hydrolyzed
[2]McIntyre Group Ltd, University Park, IL, Mackam HPL-28ULS
[3]UCARE ™ Polymer LR-400, available from Amerchol Corporation (Plaquemine, Louisiana)

A target weight of 300 grams, for each of the above compositions, is prepared with the use of a conventional overhead stirrer (IKA® RW20DZM Stirrer available from IKA® Works, Inc., Wilmington, Del.) and a hot plate (Corning Incorporated Life Sciences, Lowell, Mass.). Into an appropriately sized and cleaned vessel, the distilled water and glycerin are added with stirring at 100-150 rpm. The cationic polymer, when present, is then slowly added with constant stirring until homogenous. The polyvinyl alcohol is weighed into a suitable container and slowly added to the main mixture in small increments using a spatula while continuing to stir while avoiding the formation of visible lumps. The mixing speed is adjusted to minimize foam formation. The mixture is slowly heated to 75° C. to 80° C. after which surfactants are added. The mixture is then heated to 85° C. while continuing to stir and then allowed to cool to room temperature. Additional distilled water is added to compensate for water lost to evaporation (based on the original tare weight of the container). The final pH is between 5.2-6.6 and adjusted with citric acid or diluted sodium hydroxide if necessary. The resulting processing mixture viscosity is measured.

Examples 13-15

Dissolving Porous Shampoo Solids and Performance/Structural Data: Faster Drying and Anionic:Amphoteric Ratio Study The dissolving porous shampoo solid Examples 13, 14, and 15 were prepared from the surfactant/polymer liquid processing solutions from Examples 1, 2, and 3, respectively, as described below. Each example is comprised of 4 versions evaluating two processing variables at high and low values, namely the density (0.26 and 0.32 grams/cm³ aerated wet densities) and the drying temperature (one condition consisting of drying the Articles for 30 minutes in a 75° C. oven followed by drying overnight in a 40° C. oven versus the second condition consisting of drying the Articles for 30 to 45 minutes in a 130° C. oven).

TABLE 5

| | Ex. 13.1 | Ex. 13.2 | Ex. 13.3 | Ex. 13.4 |
|---|---|---|---|---|
| Liquid Processing Composition (Ex.) | (Ex. 1) | (Ex. 1) | (Ex. 1) | (Ex. 1) |
| Anionic:Amphoteric | 100:0 | 100:0 | 100:0 | 100:0 |
| % Solids | 28.1% | 28.1% | 28.1% | 28.1% |
| Viscosity (cp) | 5,300 | 5,300 | 5,300 | 5,300 |
| Cationic polymer | None | None | None | None |

TABLE 5-continued

| | Ex. 13.1 | Ex. 13.2 | Ex. 13.3 | Ex. 13.4 |
|---|---|---|---|---|
| Aeration Time (sec) | 35 | 25 | 35 | 25 |
| Wet Density (g/cm³) | 0.26 | 0.32 | 0.26 | 0.32 |
| Oven Temperature (° C.) | 130 | 130 | 75/40[a] | 75/40[a] |
| Drying Time (min) | 42 | 49 | 1140 | 1140 |
| Average dry Article weight (g) | 0.87 | 1.03 | 0.80 | 0.95 |
| Average dry Article thickness (cm) | 0.52 | 0.52 | 0.47 | 0.48 |
| Average dry Article density (g/cm³) | 0.10 | 0.12 | 0.10 | 0.12 |
| Average basis weight (g/m²) | 520 | 610 | 470 | 560 |

[a]Articles stored in first oven held at 75° C. for 30 minutes and then second oven held at 40° C. overnight (14 hours).

TABLE 6

| | Ex. 14.1 | Ex. 14.2 | Ex. 14.3 | Ex. 14.4 |
|---|---|---|---|---|
| Liquid Processing Composition (Ex.) | (Ex. 2) | (Ex. 2) | (Ex. 2) | (Ex. 2) |
| Anionic:Amphoteric | 80:20 | 80:20 | 80:20 | 80:20 |
| % Solids | 28.9% | 28.9% | 28.9% | 28.9% |
| Viscosity (cp) | 8,200 | 8,200 | 8,200 | 8,200 |
| Cationic polymer | None | None | None | None |
| Aeration Time (sec) | 76 | 65 | 75 | 64 |
| Wet Density (g/cm³) | 0.26 | 0.32 | 0.26 | 0.32 |
| Oven Temperature (° C.) | 130 | 130 | 75/40[a] | 75/40[a] |
| Drying Time (min) | 46 | 46 | 1210 | 1210 |
| Average dry Article weight (g) | 0.94 | 1.08 | 0.89 | 0.89 |
| Average dry Article thickness (cm) | 0.53 | 0.49 | 0.49 | 0.46 |
| Average dry Article density (g/cm³) | 0.10 | 0.13 | 0.11 | 0.11 |
| Average basis weight (g/m²) | 560 | 640 | 530 | 530 |

[a]Articles stored in first oven held at 75° C. for 30 minutes and then second oven held at 40° C. overnight (14 hours).

TABLE 7

| | Ex. 15.1 | Ex. 15.2 | Ex. 15.3 | Ex. 15.4 |
|---|---|---|---|---|
| Liquid Processing Composition (Ex.) | (Ex. 3) | (Ex. 3) | (Ex. 3) | (Ex. 3) |
| Anionic:Amphoteric | 60:40 | 60:40 | 60:40 | 60:40 |
| % Solids | 29.5% | 29.5% | 29.5% | 29.5% |
| Viscosity (cp) | 14,500 | 14,500 | 14,500 | 14,500 |
| Cationic polymer | None | None | None | None |
| Aeration Time (sec) | 125 | 95 | 120 | 85 |
| Wet Density (g/cm³) | 0.26 | 0.32 | 0.26 | 0.32 |
| Oven Temperature (° C.) | 130 | 130 | 75/40[a] | 75/40[a] |
| Drying Time (min) | 39 | 47 | 1170 | 1170 |
| Average dry Article weight (g) | 0.99 | 1.06 | 0.91 | 1.09 |
| Average dry Article thickness (cm) | 0.52 | 0.50 | 0.48 | 0.48 |
| Average dry Article density (g/cm³) | 0.11 | 0.13 | 0.11 | 0.13 |
| Average basis weight (g/m²) | 580 | 630 | 540 | 650 |

[a]Articles stored in first oven held at 75° C. for 30 minutes and then second oven held at 40° C. overnight (14 hours).

250 grams of the surfactant/polymer liquid processing solution (from Examples 1 through 3) is transferred into a 5 quart stainless steel bowl of a KITCHENAID® Mixer Model K5SS (available from Hobart Corporation, Troy, Ohio) and fitted with a flat beater attachment. The mixture is vigorously aerated at a maximum speed setting of 10 until a wet density of approximately 0.26 grams/cm³ or 0.32 grams/cm³ is achieved (times recorded in table). The density is measured by weighing a filling a cup with a known volume and evenly scraping off the top of the cup with a spatula. The resulting aerated mixture is then spread with a spatula into square 160 mm×160 mm aluminum molds with a depth of 6.5 mm with the excess wet foam being removed with the straight edge of a large metal spatula that is held at a 45° angle and slowly dragged uniformly across the mold surface. The aluminum molds are then placed into a 75° C. convection oven for approximately 30 minutes and then immediately transferred into a 40° C. convection oven for overnight. Alternatively, the aluminum molds may be placed into a 130° C. convection oven for approximately 35 to 45 minutes until the weight loss due to evaporation is between 67% and 69% of the original foam weight within each mold. The molds are allowed to cool to room temperature with the substantially dry porous solids removed from the molds with the aid of a thin spatula and tweezers.

Each of the resulting 160 mm×160 mm square pads is cut into nine 43 mm×43 mm squares (with rounded edges) using a cutting die and a Samco SB20 cutting machine (each square representing surface area of approximately 16.9 cm$^2$). The resulting smaller pads are then equilibrated overnight (14 hours) in a constant environment room kept at 70° F. and 50% relative humidity within large zip-lock bags that are left open to the room atmosphere. Each pad is then weighed and placed on an individual weight boat with the original mold side facing downward. The average pad weights are recorded.

Dissolution and Lather Volume:

The below tables summarize the hand dissolution and lather volume performance data from the dissolvable porous solid shampoos of Examples 13 through 15. The data was collected by the methods as described herein.

Dissolution/Lather Performance from Lower Density Articles

Prepared from 0.26 Wet Density Foams

TABLE 8

| Example | Anionic:Amphoteric Ratio | Drying Temperature (° C.) | Dry Density (grams/cm$^3$) | Hand Dissolution | Lather Volume |
|---|---|---|---|---|---|
| Ex. 13.1 | 100:0 | 130 | 0.10 | 12 strokes | 90 ml |
| Ex. 13.3 | 100:0 | 75/40[1] | 0.10 | >30 strokes | 85 ml |
| Ex. 14.1 | 80:20 | 130 | 0.10 | 10 strokes | 100 ml |
| Ex. 14.3 | 80:20 | 75/40[1] | 0.11 | 20 strokes | 105 ml |
| Ex. 15.1 | 60:40 | 130 | 0.11 | 4 strokes | 140 ml |
| Ex. 15.3 | 60:40 | 75/40[1] | 0.11 | 14 strokes | 120 ml |

[1] Articles stored in first oven held at 75° C. for 30 minutes and then second oven held at 40° C. overnight (14 hours)

Dissolution/Lather Performance from Higher Density Articles

Prepared from 0.32 Wet Density Foams

TABLE 9

| Example | Anionic:Amphoteric Ratio | Drying Temperature (° C.) | Dry Density (grams/cm$^3$) | Hand Dissolution | Lather Volume |
|---|---|---|---|---|---|
| Ex. 13.2 | 100:0 | 130 | 0.12 | >30 strokes | 75 ml |
| Ex. 13.4 | 100:0 | 75/40[1] | 0.12 | >30 strokes | 80 ml |
| Ex. 14.2 | 80:20 | 130 | 0.13 | 14 strokes | 105 ml |
| Ex. 14.4 | 80:20 | 75/40[1] | 0.11 | 28 strokes | 100 ml |
| Ex. 15.2 | 60:40 | 130 | 0.13 | 4 strokes | 125 ml |
| Ex. 15.4 | 60:40 | 75/40[1] | 0.13 | 30 strokes | 120 ml |

[1] Articles stored in first oven held at 75° C. for 30 minutes and then second oven held at 40° C. overnight (14 hours)

The above two data sets on both the higher and lower density porous solids comprising differing anionic:amphoteric surfactant ratios demonstrate single variably improved dissolution performance among the Articles that are dried at the higher temperature and for a shorter time period (130° C. for 30 to 45 minutes) relative to the Articles that are dried at the lower temperature and for a longer time period (75° C. for 30 minutes followed by 40° C. overnight). While not being bound to theory, this is believed to be due to the formation of a more open celled structure with a resulting higher available surface area for dissolution upon being diluted with water. Additionally, the above two data sets demonstrate single variably improved dissolution and lather performance from the Articles produced from the surfactant systems with a higher proportion of amphoteric surfactant.

Structural Characterization:

The below tables summarize the structural measurements taken on the higher and lower density porous solids from Examples 13, 14 and 15 produced from two differing drying temperatures and comprising the differing anionic:amphoteric ratios. SEM and micro-CT images were also taken for the lower density Articles and are referenced in the attached figures. The data was collected by the methods as described herein.

Structural Measurements from Lower Density Articles

Prepared from 0.26 Wet Density Foams

TABLE 10

Figure 1B:
FIG. 1b SEM Images of Example 13.3.
Figure 1C:
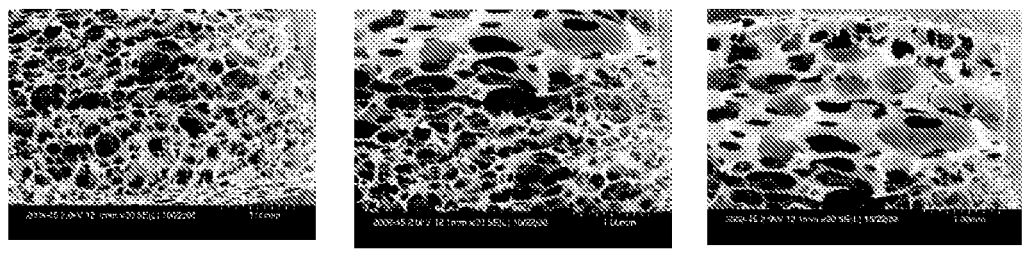
FIG. 1c SEM Images of Example 14.1.
Figure 1D:
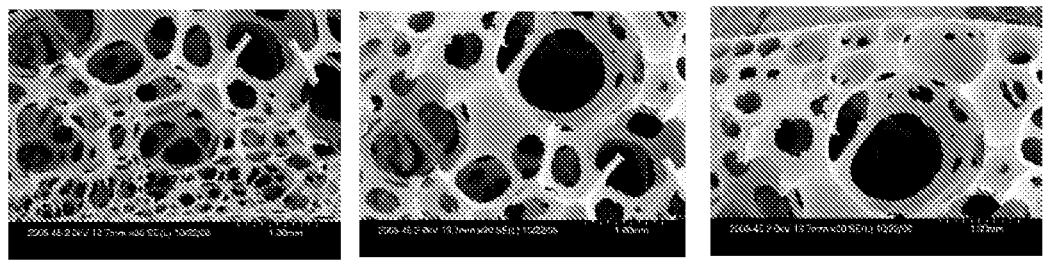
FIG. 1d SEM Images of Example 14.3.
Figure 1E:
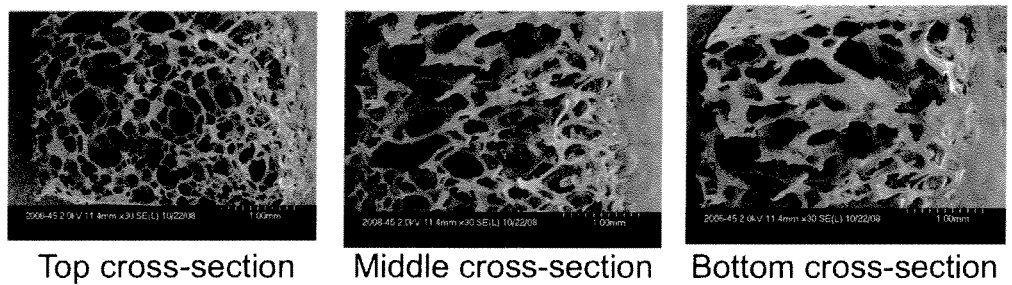
FIG. 1e SEM Images of Example 15.1.
Figure 1F:
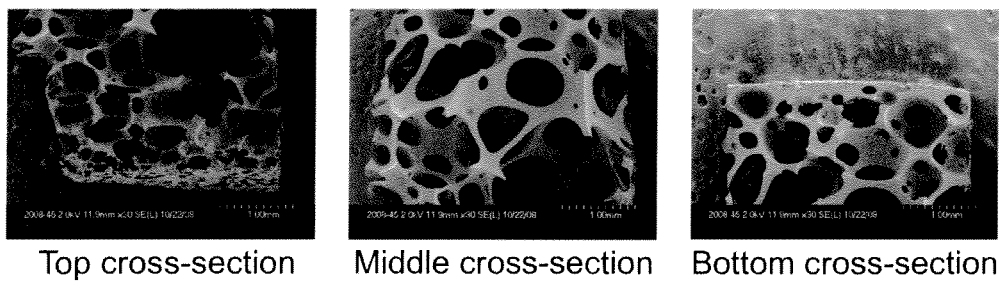
FIG. 1f SEM Images of Example 15.3.
Figure 2A:
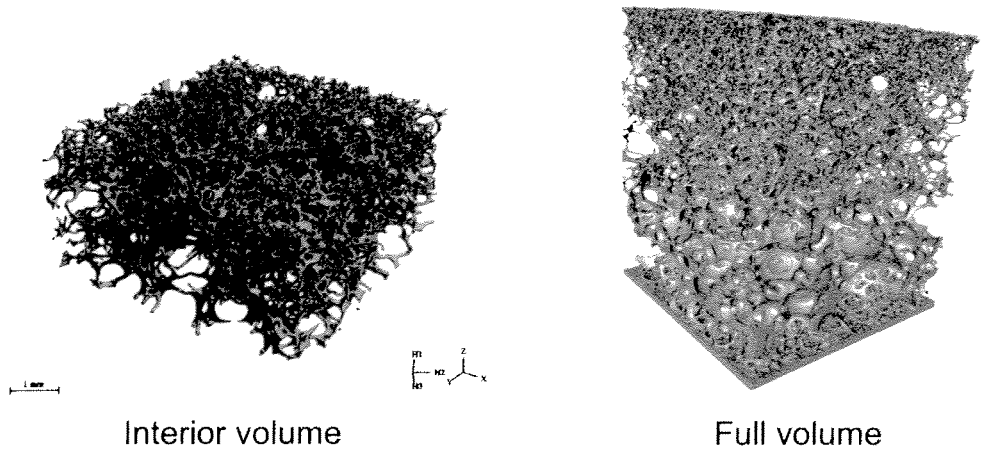
FIG. 2a Micro-CT Images of Example 13.1.
Figure 2B:
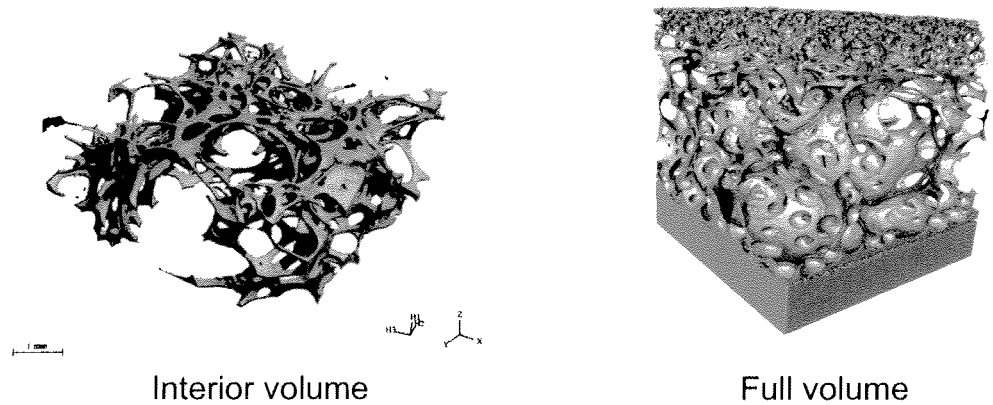
FIG. 2b Micro-CT Images of Example 13.3.
Figure 2C:
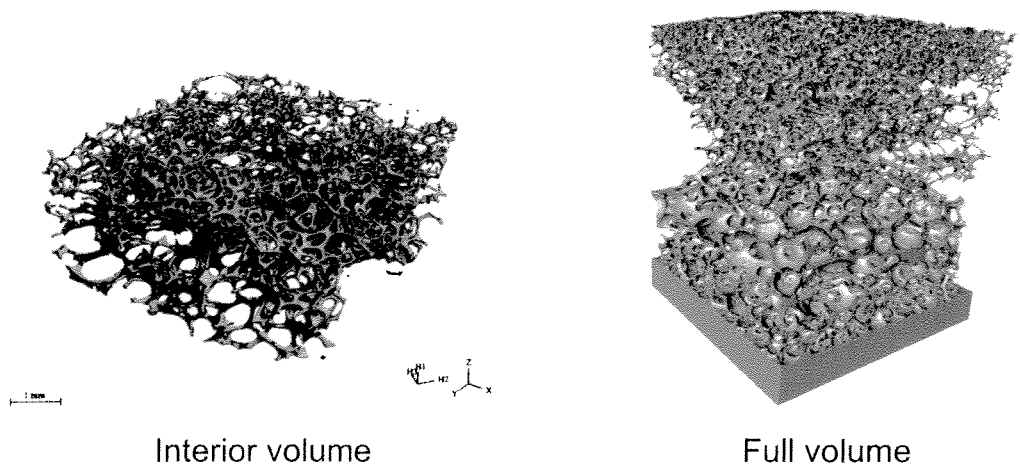
FIG. 2c Micro-CT Images of Example 14.1.
Figure 2D:
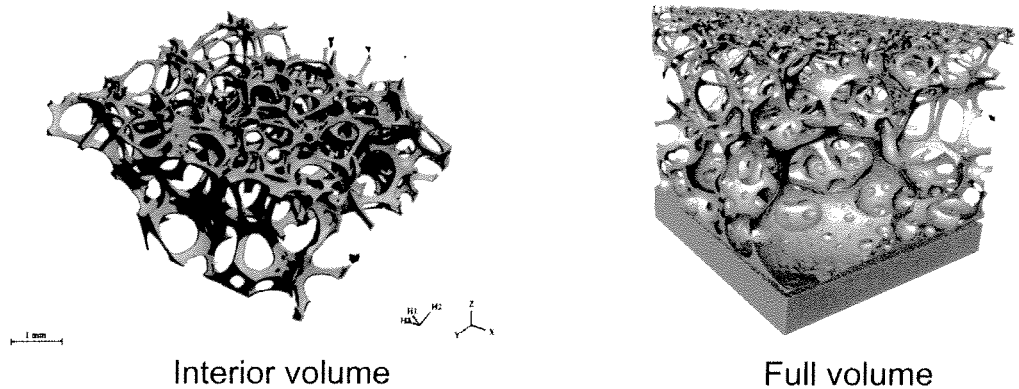
FIG. 2d Micro-CT Images of Example 14.3.
Figure 2E:
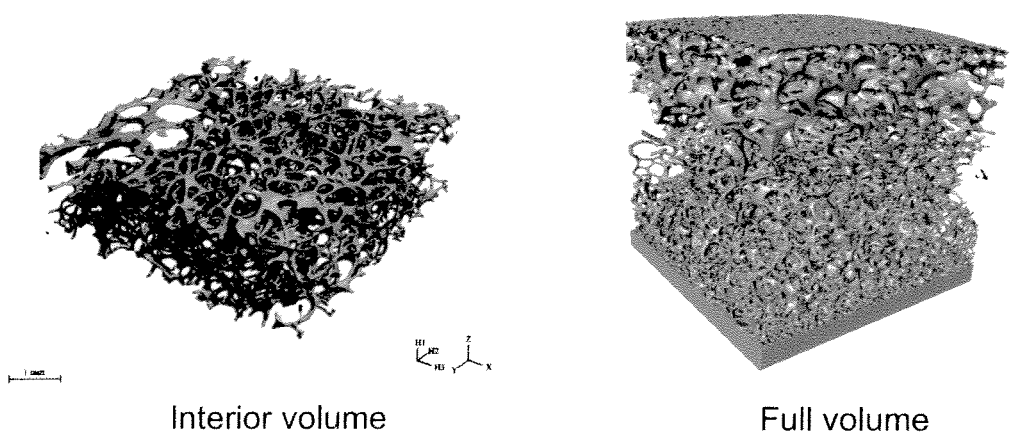
FIG. 2e Micro-CT Images of Example 15.1.
Figure 2F:
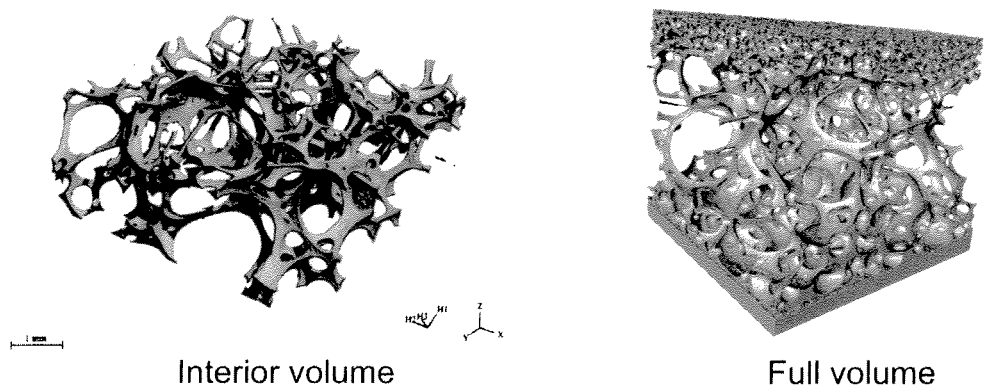
FIG. 2f Micro-CT Images of Example 15.3.

| Example | Kr BET Surface Area (m$^2$/g) | Pycnometry % Open Cells | Micro-CT Cell Wall thickness (mm) | Micro-CT Star Volume (mm$^3$) | Micro-CT SMI Index | SEM Image | CT Image |
|---|---|---|---|---|---|---|---|
| Ex. 13.1 | 0.096 | 91.0% | 0.041 | 7.5 | 2.3 | FIG. 1a | FIG. 2a |
| Ex. 13.3 | 0.079 | 89.7% | 0.086 | 13.4 | 1.2 | FIG. 1b | FIG. 2b |
| Ex. 14.1 | 0.047 | 90.7% | 0.050 | 11.1 | 2.4 | FIG. 1c | FIG. 2c |
| Ex. 14.3 | 0.030 | 92.1% | 0.089 | 10.8 | 1.5 | FIG. 1d | FIG. 2d |
| Ex. 15.1 | 0.051 | 92.0% | 0.062 | 5.7 | 2.4 | FIG. 1e | FIG. 2e |
| Ex. 15.3 | 0.039 | 93.6% | 0.088 | 12.3 | 1.5 | FIG. 1f | FIG. 2f |

Structural Measurements from Lower Density Articles

Prepared from 0.32 Wet Density Foams

TABLE 11

Figure 3A:
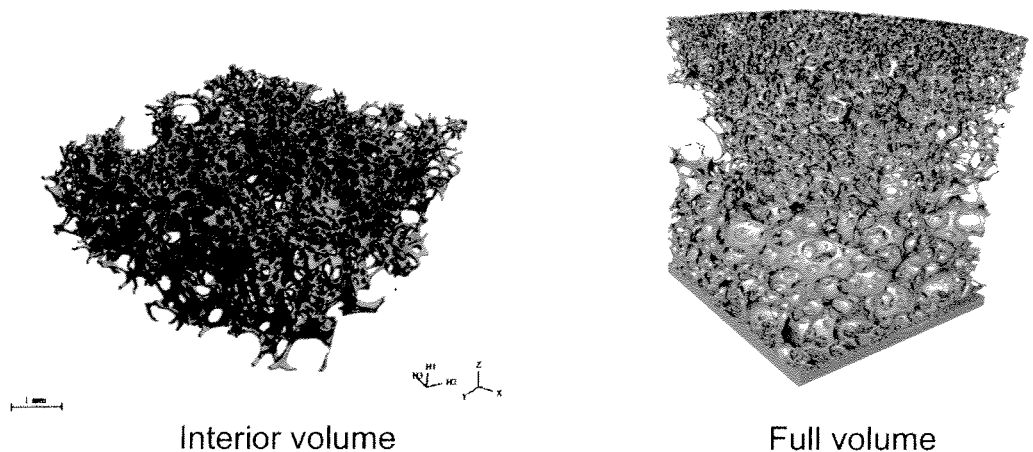
FIG. 3a Micro-CT Images of Example 13.2.
Figure 3B:
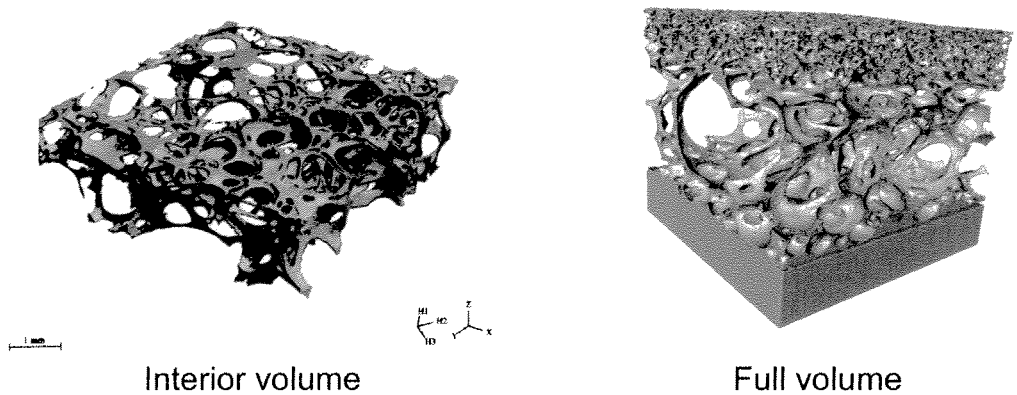
FIG. 3b Micro-CT Images of Example 13.4.
Figure 3C:
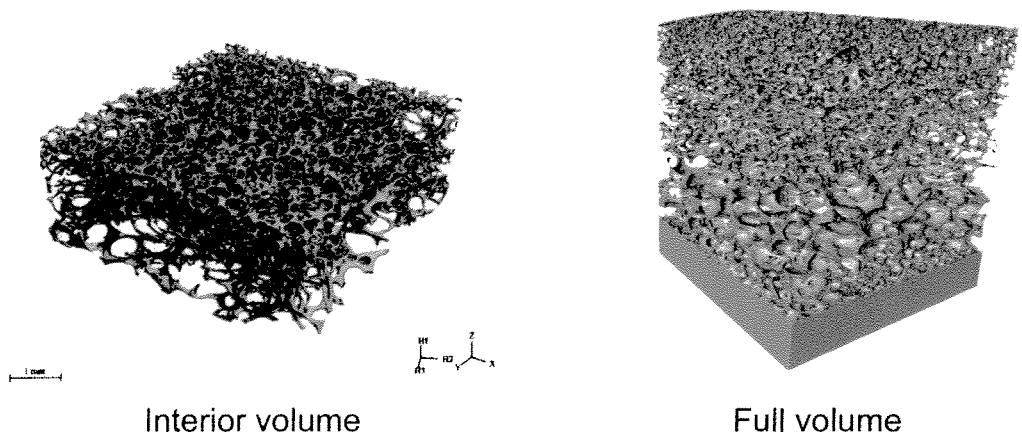
FIG. 3c Micro-CT Images of Example 14.2.
Figure 3D:
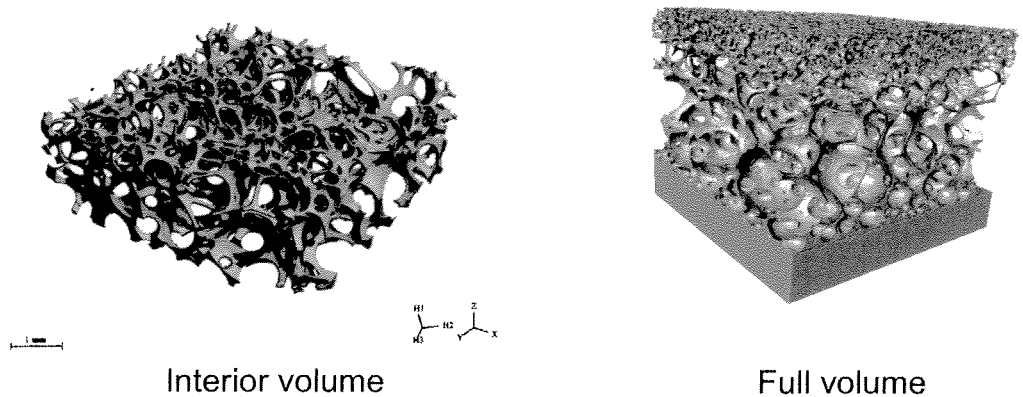
FIG. 3d Micro-CT Images of Example 14.4.
Figure 3E:
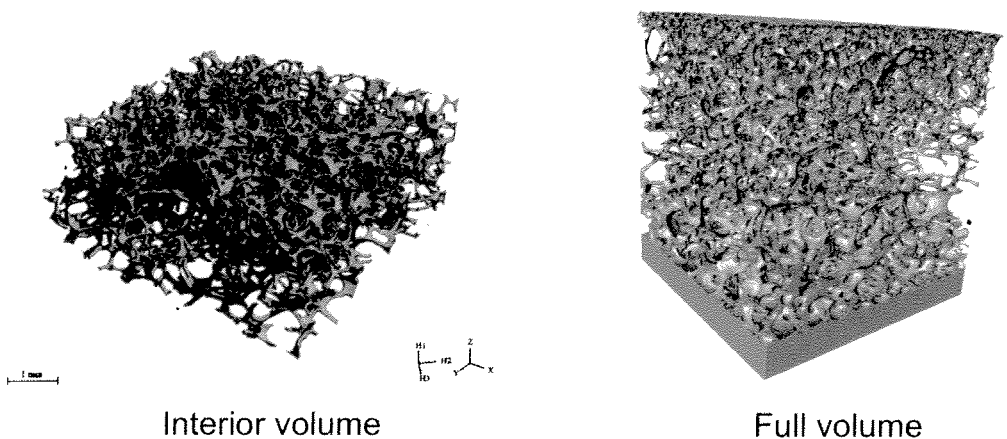
FIG. 3e Micro-CT Images of Example 15.2.
Figure 3F:
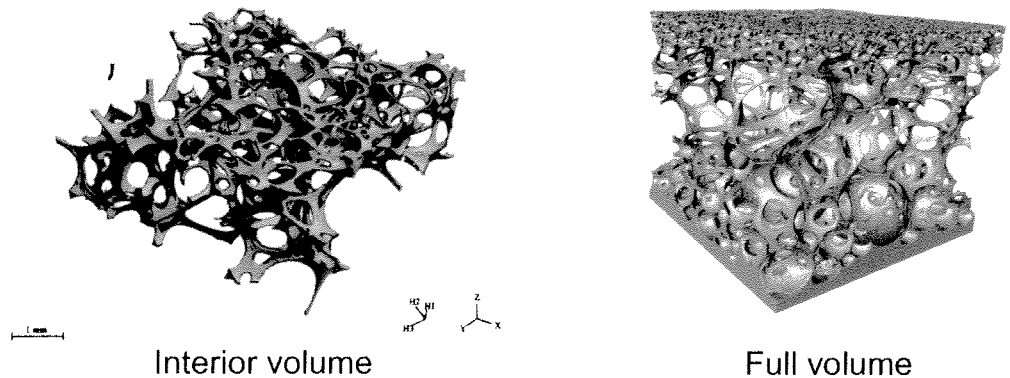
FIG. 3f Micro-CT Images of Example 15.4.

| Example | Kr BET Surface Area (m²/g) | Pycnometry % Open Cells | Micro-CT Cell Wall thickness (mm) | Micro-CT Star Volume (mm³) | Micro-CT SMI Index | µCT Image |
|---|---|---|---|---|---|---|
| Ex. 13.2 | 0.073 | 89.1% | 0.044 | 8.5 | 2.2 | FIG. 3a |
| Ex. 13.4 | 0.050 | 90.5% | 0.088 | 10.2 | 1.1 | FIG. 3b |
| Ex. 14.2 | 0.044 | 90.6% | 0.047 | 4.4 | 2.5 | FIG. 3c |
| Ex. 14.4 | 0.036 | 89.4% | 0.080 | 4.7 | 1.2 | FIG. 3d |
| Ex. 15.2 | 0.049 | 92.4% | 0.060 | 7.2 | 2.4 | FIG. 3e |
| Ex. 15.4 | 0.033 | 88.3% | 0.084 | 12.2 | 1.6 | FIG. 3f |

The above two data sets on both the higher and lower density porous solids comprising differing anionic:amphoteric surfactant ratios demonstrate single variably increased BET specific surface areas, decreased Cell wall thicknesses, and higher SMI Index values among the Articles that are dried at the higher temperature and for a shorter time period (130° C. for 30 to 45 minutes—See Examples 13.1, 14.1, 15.1, 13.2, 14.2 and 15.2) relative to the Articles that are dried at the lower temperature and for a longer time period (75° C. for 30 minutes followed by 40° C. overnight approx. 14 hours—See Examples 13.3, 14.3, 15.3, 13.4, 14.4 and 15.4). Specifically, one can see 22% to 57% increased BET surface areas, 29% to 52% reduced Cell Wall thicknesses, and SMI Index values that are 1 unit higher by comparing across similar compositions and densities (See Examples 13.1 vs. 13.3, 14.1 vs. 14.3, 15.1 vs. 15.3, 13.2 vs. 13.4, 14.2 vs. 14.4, and 15.2 vs. 15.4). The SEM and Micro-CT images are qualitatively consistent with this data (See FIGS. 1a vs. 1b, 1c vs. 1d, 1e vs. 1f, 2a vs. 2b, 2c vs. 2d, 2e vs. 2f, 3a vs. 3b, 3c vs. 3d, and 3e vs. 3f).

In several instances the Articles dried at the lower temperatures exhibit increased Star Volumes and % Open Cells. While not being bound to theory, this is believed to be due to increased drainage and bubble coalescence in the inner volume region (the selected region for the Micro-CT computations) which leads to a denser lower region that is believed to serve as a rate limiting barrier for water diffusion and rapid dissolution. This phenomenon can be observed qualitatively by viewing the Middle Cross-section and Bottom Cross-section SEM images (See FIGS. 1a vs. 1b, 1c vs. 1d, and 1e vs. 1f) as well as the Interior Volume and Full Volume Micro-CT images (See FIGS. 2a vs. 2b, 2c vs. 2d, 2e vs. 2f, 3a vs. 3b, 3c vs. 3d, and 3e vs. 3f).

Examples 16-19

Dissolving Porous Shampoo Solids and Performance Data: Liquid Processing % Solids and Viscosity Study The dissolving porous shampoo solid Examples 16, 17, 18, and 19 were prepared from the surfactant/polymer liquid processing solutions from Examples 3, 4, 5, and 6, respectively, and according to the same procedure as described for Examples 13 through 15 (employing a 130° C. drying temperature for 30-45 minutes). These porous solid examples are produced from liquid processing compositions with identical components and in identical polymer:surfactant:placticizer ratios, the only difference being the level of water giving rise to increasing % solids and corresponding increasing processing mixture viscosities. For the liquid processing compositions with higher % solids and viscosities, extended aeration times are explored in an attempt to achieve the requisite density range of the present invention.

TABLE 12

| | Ex. 16 | Ex. 17.1 | Ex. 17.2 | Ex. 17.3 |
|---|---|---|---|---|
| Liquid Processing Composition (Ex.) | (Ex. 3) | (Ex. 4) | (Ex. 4) | (Ex. 4) |
| Anionic:Amphoteric (Zwitterionic) | 60:40 | 60:40 | 60:40 | 60:40 |
| % Solids | 29.5% | 33.0% | 33.0% | 33.0% |
| Viscosity (cp) | 14,500 | 23,900 | 23,900 | 23,900 |
| Cationic polymer | None | None | None | None |
| Aeration Time (sec) | 125 | 105 | 140 | 155 |
| Wet Density (g/cm³) | 0.26 | 0.38 | 0.33 | 0.35 |
| Oven Temperature (° C.) | 130 | 130 | 130 | 130 |
| Drying Time (min) | 40 | 52 | 45 | 52 |
| Average dry pad weight (g) | 0.99 | 1.54 | 1.27 | 1.35 |
| Average dry pad thickness (cm) | 0.52 | 0.43 | 0.46 | 0.51 |
| Average dry pad density (g/cm³) | 0.11 | 0.21 | 0.16 | 0.16 |
| Average basis weight (g/cm²) | 580 | 910 | 750 | 800 |

TABLE 13

| | Ex. 18.1 | Ex. 18.2 | Ex. 18.3 | Ex. 19 |
|---|---|---|---|---|
| Liquid Processing Composition (Ex.) | (Ex. 5) | (Ex. 5) | (Ex. 5) | (Ex. 6) |
| Anionic:Amphoteric (Zwitterionic) | 60:40 | 60:40 | 60:40 | 60:40 |
| % Solids | 36.0% | 36.0% | 36.0% | 39.0% |
| Viscosity (cp) | 37,600 | 37,600 | 37,600 | 51,000 |
| Cationic polymer | None | None | None | None |
| Aeration Time (sec) | 100 | 150 | 360 | 480 |
| Wet Density (g/cm³) | 0.44 | 0.40 | 0.38 | 0.52 |
| Oven Temperature (° C.) | 130 | 130 | 130 | 130 |
| Drying Time (min) | 55 | 50 | 60 | 85 |
| Average dry pad weight (g) | 1.75 | 1.81 | 1.63 | 2.73 |
| Average dry pad thickness (cm) | 0.50 | 0.52 | 0.53 | 0.53 |
| Average dry pad density (g/cm³) | 0.21 | 0.21 | 0.18 | 0.31 |
| Average basis weight (g/cm²) | 1040 | 1070 | 960 | 1600 |

The above table demonstrates the technical difficulty in achieving the requisite density and basis weight range of the present invention at higher % solids and viscosity levels. In particular, increasing the % solids level from 29.5% to 33% resulted in a viscosity increase from 14,500 cps to 23,900 cps. In this instance, increasing the aeration time is successful in achieving a desired lower density resulting in a lower wet and dry density limit of approximately 0.33 g/cm³ and 0.16 g/cm³, respectively (See Example 16 vs. Examples 17.1, 17.2, and 17.3). Increasing the % solids level further to 36% resulted in a viscosity of 37,600 cps. Increasing the aeration time to 380 seconds was only able to achieve a resulting lower wet and dry density of approximately 0.38 g/cm³ and 0.18-0.21 g/cm³, respectively (See Examples 18.1, 18.2 and 18.3). A further increase in % solids level to 39% resulted in a viscosity of 51,000 cps with a resulting lower wet and dry density limit of approximately 0.52 g/cm₃ and 0.31 g/cm³, respectively (See Example 19). It has generally been found that viscosities of below 30,000 cps are required to achieve the open-celled solids with the defined requisite wet and dry densities of the present invention with conventional processing as is demonstrated above.

Dissolution Performance:

The below tables summarize the hand dissolution performance data from the dissolvable porous solid shampoos of Examples 16 through 19. The data was collected by the methods as described herein.

TABLE 14

| Example | % Solids | Viscosity (cp) | Aeration Time (sec) | Dry Density (grams/cm³) | Hand Dissolution |
|---------|----------|----------------|---------------------|--------------------------|------------------|
| Ex. 16  | 29.5%    | 14,500         | 125                 | 0.11                     | 4 strokes        |
| Ex. 17.1| 33.0%    | 23,900         | 105                 | 0.21                     | 16 strokes       |
| Ex. 17.2| 33.0%    | 23,900         | 140                 | 0.17                     | 14 strokes       |
| Ex. 17.3| 33.0%    | 23,900         | 155                 | 0.16                     | 6 strokes        |
| Ex. 18.1| 36.0%    | 37,600         | 100                 | 0.21                     | 30 strokes       |
| Ex. 18.2| 36.0%    | 37,600         | 150                 | 0.21                     | 30 strokes       |
| Ex. 18.3| 36.0%    | 37,600         | 360                 | 0.18                     | 24 strokes       |
| Ex. 19  | 39.0%    | 51,000         | 480                 | 0.31                     | >30 strokes      |

The above table demonstrates an upper limit on liquid processing mixture % solids and viscosity level in order to achieve fast dissolving porous structures of the present invention (according to conventional processing). In particular, the liquid processing mixtures with 36% and 39% solids levels and corresponding high viscosities resulted in porous solids with poor dissolution performance (See Examples 18.1, 18.2, 18.3 and 19). In contrast, the liquid processing mixtures with 29.5% and 33.0% solids levels and corresponding lower viscosities resulted in porous solids with good dissolution performance (less than 20 strokes). Examples 16 through 19 demonstrate the inherent technical difficulty of achieving fast dissolving porous solids of the present invention at higher % solids and viscosity levels based on conventional processing.

Examples 20-26

Dissolving Porous Shampoo Solids—Hot vs. Ambient Processing

The dissolving porous shampoo solid Examples 20-26 are prepared from the surfactant/polymer liquid processing solutions from Examples 7, 8, 9, 10, 11 and 12, respectively. The examples designated as "Ambient Processing" conditions are prepared according to the same procedure as described for Examples 13 through 19 (employing a 130 degrees Celsius drying temperature for 30-45 minutes). The examples designated as "Hot Processing" conditions are made in the same manner except that the liquid processing mixture is preheated to 70° C. before aeration and a 70-75° C. hot water jacket is employed around the 5 quart stainless steel bowl of the KITCHENAID® Mixer Model K5SS (available from Hobart Corporation, Troy, Ohio) during the aeration part of the process (also employing a 130° C. drying temperature for 30-45 minutes). The porous solid examples within each Table are produced from liquid processing compositions with identical components and in the same polymer:surfactant:placticizer ratios, the only difference being the level of water giving rise to increasing % solids and corresponding increasing processing mixture viscosities. Examples 20 through 24 comprise a cationic guar polymer and examples 25 and 26 comprise a cationic cellulose polymer.

TABLE 15

|  | Ex. 20.1 | Ex. 20.2 | Ex. 21.1 | Ex. 21.2 |
|---|---|---|---|---|
| Liquid Processing Composition (Ex.) | (Ex. 7) | (Ex. 7) | (Ex. 8) | (Ex. 8) |
| Anionic:Amphoteric (Zwitterionic) | 60:40 | 60:40 | 60:40 | 60:40 |
| % Solids | 30.1% | 30.1% | 33.3% | 33.3% |
| Viscosity (cp) | 19,200 | 19,200 | 32,200 | 32,200 |
| Cationic polymer | Guar | Guar | Guar | Guar |
| Processing Conditions | Ambient | Ambient | Ambient | Ambient |
| Aeration Time (sec) | 105 | 160 | 105 | 150 |
| Wet Density (g/cm³) | 0.32 | 0.29 | 0.38 | 0.32 |
| Oven Temperature (° C.) | 130 | 130 | 130 | 130 |
| Drying Time (min) | 49 | 40 | 47 | 40 |
| Average dry pad weight (g) | 1.08 | 0.94 | 1.42 | 1.21 |
| Average dry pad thickness (cm) | 0.41 | 0.40 | 0.48 | 0.45 |
| Average pad shrinkage (%) | 37% | 38% | 27% | 30% |
| Average dry pad density (g/cm³) | 0.16 | 0.14 | 0.18 | 0.16 |
| Average basis weight (g/cm²) | 640 | 550 | 840 | 720 |

TABLE 16

|  | Ex. 21.3 | Ex. 22 | Ex. 23 | Ex. 24 |
|---|---|---|---|---|
| Liquid Processing Composition (Ex.) | (Ex. 8) | (Ex. 8) | (Ex. 9) | (Ex. 10) |
| Anionic:Amphoteric (Zwitterionic) | 60:40 | 60:40 | 60:40 | 60:40 |
| % Solids | 33.3% | 33.3% | 35.2% | 37.2% |
| Viscosity (cp) | 32,200 | 32,200 | 52,400 | 64,900 |
| Cationic polymer | Guar | Guar | Guar | Guar |
| Processing Conditions | Ambient | Hot | Hot | Hot |
| Aeration Time (sec) | 240 | 75 | 80 | 100 |
| Wet Density (g/cm³) | 0.31 | 0.28 | 0.26 | 0.32 |
| Oven Temperature (° C.) | 130 | 130 | 130 | 130 |
| Drying Time (min) | 45 | 41 | 40 | 45 |
| Average dry pad weight (g) | 1.21 | 1.21 | 1.25 | 1.56 |
| Average dry pad thickness (cm) | 0.47 | 0.57 | 0.60 | 0.55 |
| Average pad shrinkage (%) | 28% | 12% | 8% | 16% |
| Average dry pad density (g/cm³) | 0.15 | 0.13 | 0.12 | 0.17 |
| Average basis weight (g/cm²) | 720 | 720 | 740 | 920 |

TABLE 17

|  | Ex. 25 | Ex. 26 |
|---|---|---|
| Liquid Processing Composition (Ex.) | (Ex. 11) | (Ex. 12) |
| Anionic:Amphoteric (Zwitterionic) | 60:40 | 60:40 |
| % Solids | 30.1% | 33.3% |
| Viscosity (cp) | 19,600 | 35,400 |
| Cationic polymer | Cellulose | Cellulose |
| Processing Conditions | Ambient | Hot |
| Aeration Time (sec) | 120 | 130 |
| Wet Density (g/cm³) | 0.27 | 0.26 |
| Oven Temperature (° C.) | 130 | 130 |
| Drying Time (min) | 42 | 38 |
| Average dry pad weight (g) | 0.92 | 1.07 |
| Average dry pad thickness (cm) | 0.44 | 0.58 |
| Average pad shrinkage (%) | 32% | 12% |
| Average dry pad density (g/cm³) | 0.12 | 0.11 |
| Average basis weight (g/cm²) | 550 | 630 |

Dissolution Performance:

The below tables summarize the hand dissolution performance data from the dissolvable porous solid shampoos of Examples 20 through 25. The data was collected by the methods as described herein.

TABLE 18

| Example | % Solids | Visc. (cp) | Process. Condit. | Aeration Time (sec) | Dry Density (g/cm³) | % Shrinkage | Hand Dissolution |
|---|---|---|---|---|---|---|---|
| Ex. 20.1 | 30.1% | 19,200 | Ambient | 105 | 0.16 | 37% | 10 strokes |
| Ex. 20.2 | 30.1% | 19,200 | Ambient | 160 | 0.14 | 38% | 8 strokes |
| Ex. 21.1 | 33.3% | 32,200 | Ambient | 105 | 0.18 | 27% | 24 strokes |
| Ex. 21.2 | 33.3% | 32,200 | Ambient | 150 | 0.16 | 30% | 14 strokes |
| Ex. 21.3 | 33.3% | 32,200 | Ambient | 240 | 0.15 | 28% | 12 strokes |
| Ex. 22 | 33.3% | 32,200 | Hot | 75 | 0.13 | 12% | 9 strokes |
| Ex. 23 | 35.2% | 52,400 | Hot | 80 | 0.12 | 8% | 8 strokes |
| Ex. 24 | 37.2% | 64,900 | Hot | 100 | 0.17 | 16% | 10 strokes |
| Ex. 25 | 30.1% | 19,600 | Ambient | 120 | 0.12 | 32% | 9 strokes |
| Ex. 26 | 33.3% | 35,400 | Hot | 130 | 0.11 | 12% | 6 strokes |

The above examples demonstrates the use of the optional pre-heating step in the processing technique described above which enables the flexible dissolving porous solid structures prepared from pre-mixtures with higher % solids and viscosity levels (at 25° C.). In particular, rapid dissolving structures (6 to 10 strokes) were achieved with % solids levels ranging from 33.3% to 37.2% and viscosities ranging from 32,200 cps to 64,900 cps (at 25° C.) (See Examples 22, 23, 24, and 26).

These hot processed Articles demonstrate equal to better dissolution performance relative to the conventional processing of more dilute liquid processing mixtures with lower viscosities (at 25° C.) (See Examples 20.1, 20.2, 21.1, 21.2 and 21.3). This is in marked contrast to the above described examples 18 and 19 based on conventional processing techniques wherein solids levels of 36% to 39% and viscosities of 37,600 cps to 51,000 cps (at 25° C.) resulted in slowly dissolving solids (24 to >30 strokes). Additionally, the optional pre-heating process step results in Articles that under go significantly less pad shrinkage during the drying process (about 8% to about 16% versus conventional about 27% to about 38%) giving rise to improve pad appearance and properties.

Structural Characterization:

The below table summarize the structural measurements taken on the porous solids from Examples 21, 22 and 24 as representative examples for both ambient and hot processing conditions. The data was collected by the methods as described herein.

Structural Measurements Comparing Ambient versus Hot Processing

One can see from the above examples that the Articles produced by hot processing (pre-heating the premixture) of processing mixtures with high % solids levels (33% and 37%) and corresponding high viscosities (32,200 cps and 64,900 cps) result in porous structures with greater BET Specific Surface Areas representing an average 22% increase in surface area (See Examples 21.1 and 21.2 vs. Examples 22 and 24). One can also see that even the Article produced from a processing mixture with 37% solids and 64,900 cps viscosity (Example 24) exhibits structural parameters (% Open Cells, Cell Wall Thickness, Star Volume and SMI Index) within the scope of the present invention. The SEM and Micro-CT images are qualitatively consistent with this data (See FIGS. 4a and 4b vs. FIGS. 4c and 4d and See FIGS. 5a and 5b vs. FIGS. 5c and 5d).

Example 27

Dissolving Porous Shampoo Solid—Microwave Drying

An identical surfactant-polymer premix is prepared as described in Example 2 and aerated in accordance with the details given in the preparation of the Article from Example 14.1 to give Example 27. However, unlike Example 14.1 which is dried within a convection oven at 130° C., Example 27 is dried within a low energy density microwave applicator operated at a power of 2.0 kW and a belt speed of 1 foot per minute and a surrounding air temperature of 130° C. The microwave drying is conducted on equipment provided by Industrial Microwave Systems Inc. (North Carolina). The resulting Article is compared to Example 14.1 in the below table:

TABLE 19

Figure 4A:
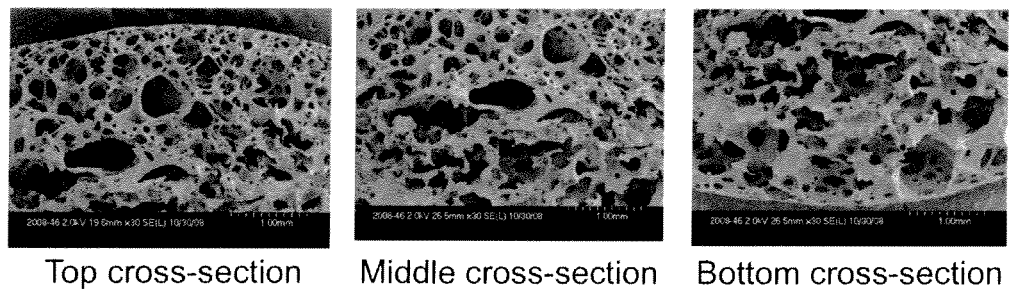
FIG. 4a SEM Images of Example 21.1.
Figure 4B:
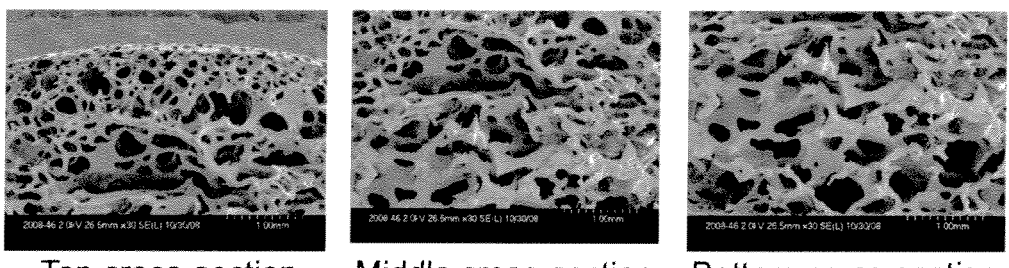
FIG. 4b SEM Images of Example 21.2.
Figure 4C:
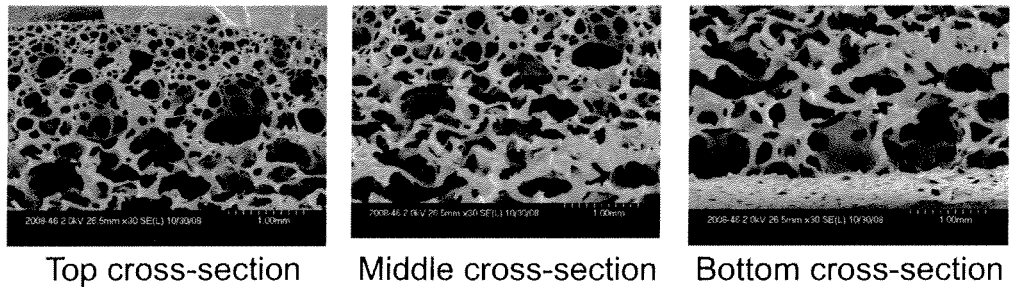
FIG. 4c SEM Images of Example 22.
Figure 4D:
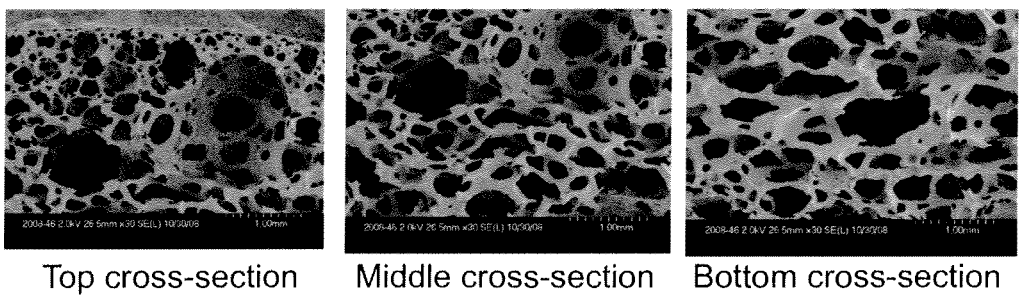
FIG. 4d SEM Images of Example 24.
Figure 5A:
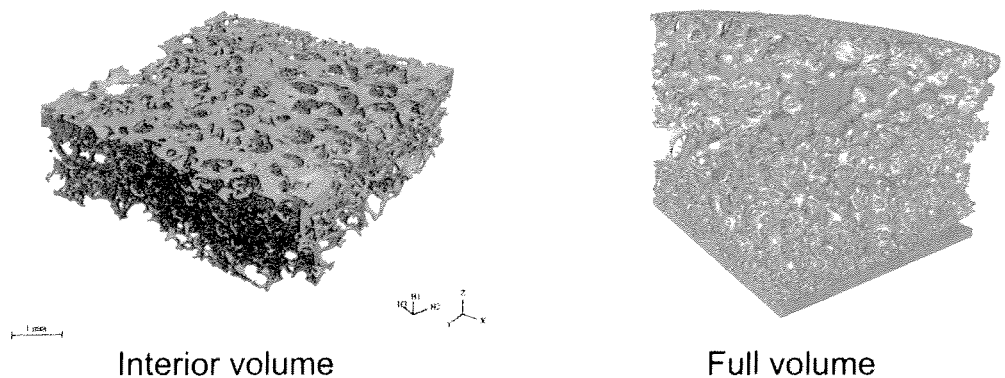
FIG. 5a Micro-CT Images of Example 21.1.
Figure 5B:
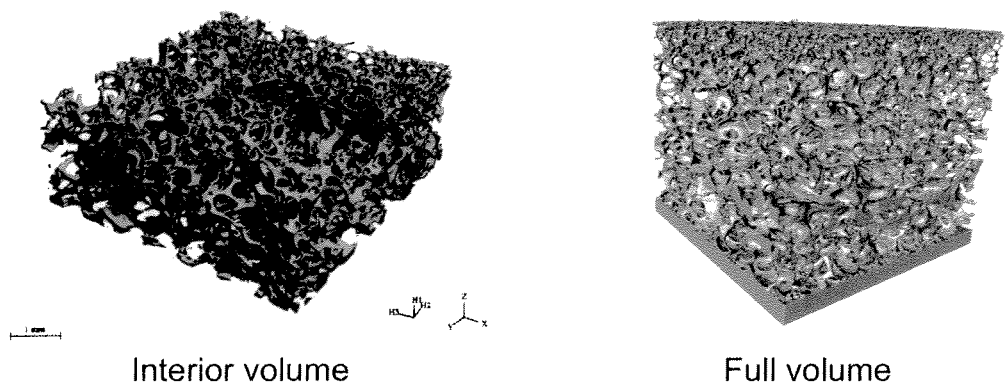
FIG. 5b Micro-CT Images of Example 21.2.
Figure 5C:
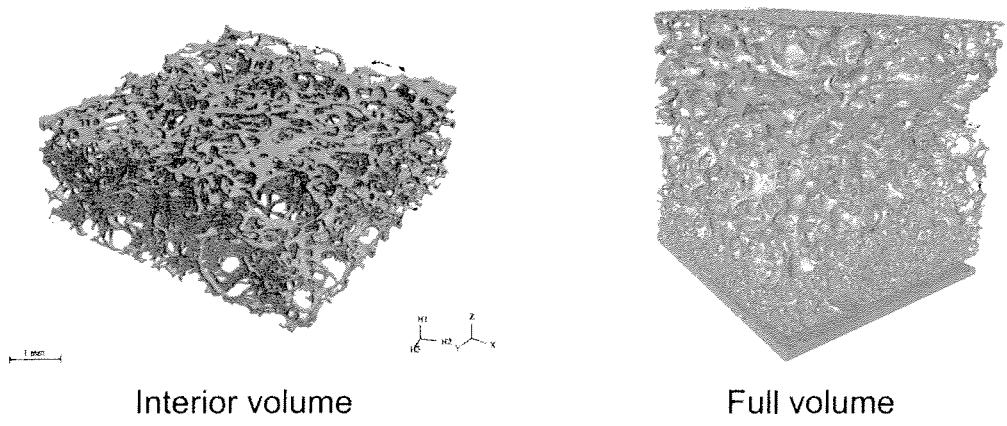
FIG. 5c Micro-CT Images of Example 22.
Figure 5D:
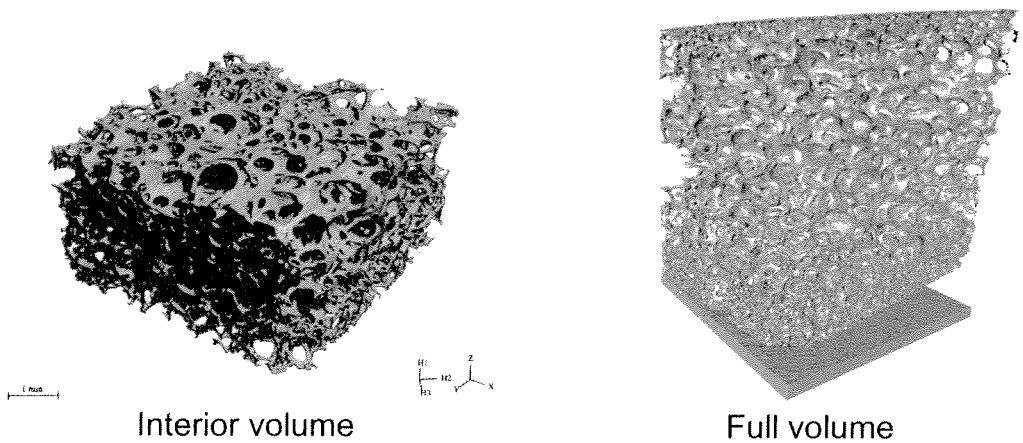
FIG. 5d Micro-CT Images of Example 24.

| Ex. | Process Condit. | Kr BET Surface Area (m²/g) | Pycnometry % Open Cells | Micro-CT Cell Wall thickness (mm) | Micro-CT Star Volume (mm³) | Micro-CT SMI Index | SEM Image | μCT Image |
|---|---|---|---|---|---|---|---|---|
| Ex. 21.1 | Ambient | 0.036 | 87.1% | 0.094 | 1.5 | 2.2 | FIG. 4a | FIG. 5a |
| Ex. 21.2 | Ambient | 0.037 | 92.3% | 0.070 | 3.9 | 2.0 | FIG. 4b | FIG. 5b |
| Ex. 22 | Hot | 0.043 | 89.8% | 0.065 | 3.6 | 2.0 | FIG. 4c | FIG. 5c |
| Ex. 24 | Hot | 0.047 | 89.8% | 0.075 | 2.5 | 1.2 | FIG. 4d | FIG. 5d |

TABLE 20

|  | Ex. 14.1 | Ex. 27 |
|---|---|---|
| Liquid Processing Composition (Ex.) | (Ex. 2) | (Ex. 2) |
| Anionic:Amphoteric | 80:20 | 80:20 |
| % Solids | 28.9% | 28.9% |
| Viscosity (cp) | 8,200 | 8,200 |
| Cationic polymer | None | None |
| Aeration Time (sec) | 76 | 75 |
| Wet Density (g/cm$^3$) | 0.26 | 0.26 |
| Drying Method | Convection Oven | Low Energy Density Microwave |
| Drying Conditions | 130° C. Air temp. | 2.0 kW 54.4° C. Air temp. |
| Drying Time (min) | 46 | 12 |
| Average dry Article weight (g) | 0.94 | 0.89 |
| Average basis weight (g/cm$^2$) | 560 | 530 |

The performance data on these two Articles comparing convection oven drying to microwave drying are given in the below table.

Dissolution/Lather Performance from Microwave vs. Convection Oven Drying

Prepared from 0.26 Wet Density Foams

TABLE 21

| Example | Anionic:Amphoteric Ratio | Drying Method | Drying Time (min) | Hand Dissolution | Lather Volume |
|---|---|---|---|---|---|
| Ex. 14.1 | 80:20 | Convection Oven | 46 | 10 strokes | 100 ml |
| Ex. 27 | 80:20 | Microwave | 12 | 6 strokes | 107 ml |

The structural measurements on these two Articles comparing convection oven drying to microwave drying are given in the below table.

Structural Measurements Comparing Ambient Versus Hot Processing

TABLE 22

Figure 6A:
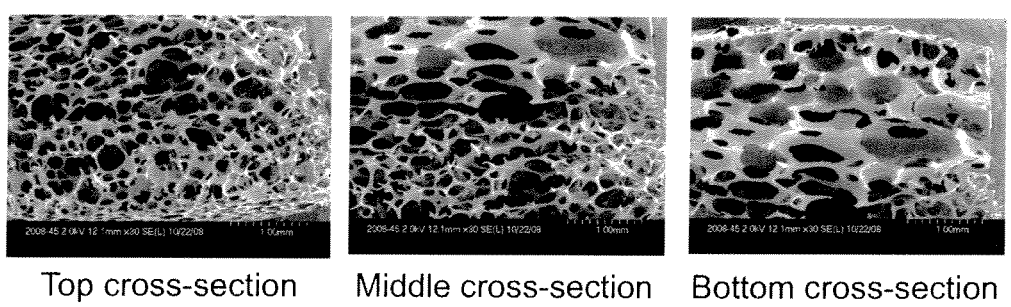
FIG. 6a SEM Images of Example 14.1.
Figure 6B:
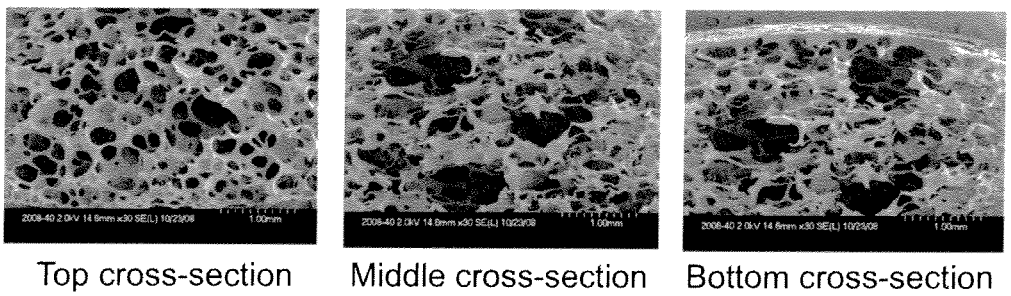
FIG. 6*b* SEM Images of Example 27.
Figure 7A:
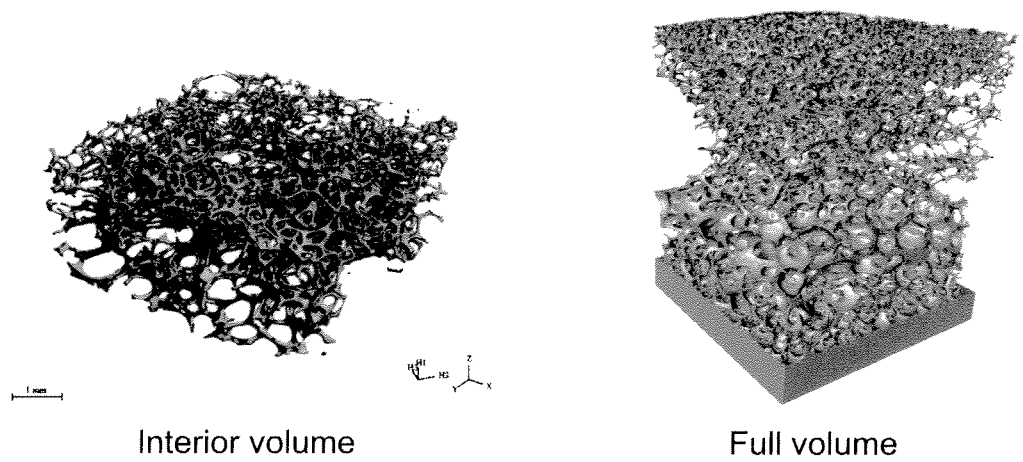
FIG. 7*a* Micro-CT Images of Example 14.1.
Figure 7B:
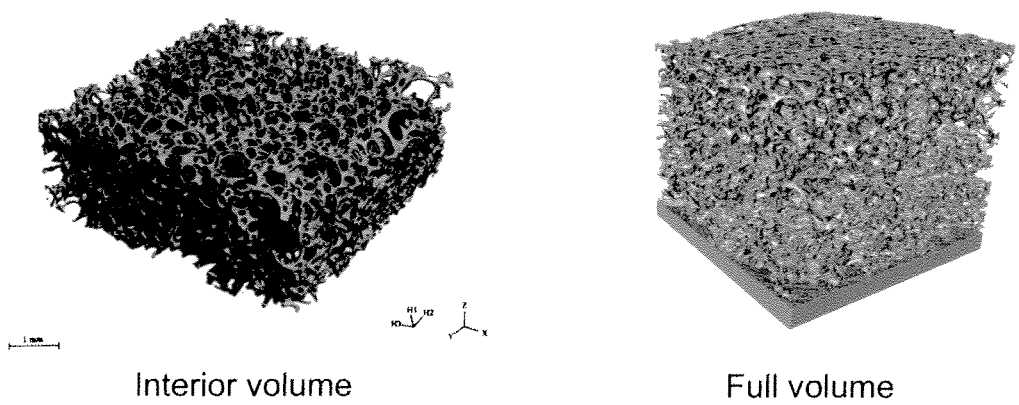
FIG. 7*b* Micro-CT Images of Example 27.

| Example | Kr BET Surface Area (m$^2$/g) | Pycnometry % Open Cells | Micro-CT Cell Wall thickness (mm) | Micro-CT Star Volume (mm$^3$) | Micro-CT SMI Index | SEM Image | μCT Image |
|---|---|---|---|---|---|---|---|
| Ex. 14.1 | 0.047 | 90.7% | 0.050 | 11.1 | 1.9 | FIG. 6a | FIG. 7a |
| Ex. 27 | 0.046 | 91.2% | 0.050 | 0.95 | 2.4 | FIG. 6b | FIG. 7b |

From Tables 21 and 22 it can be seen that microwave drying offers improvements in drying time and dissolution rate. Moreover, from Table 23 it can be seen that the Microwave drying produces Articles with the desired structural parameters within the range of the present invention. One notable difference is the significantly reduced Star Volume from the Microwave drying. While not being bound to theory, this is believed to be due to a more even cross-sectional structure arising from the simultaneous internal structure Microwave heating versus the initial surface heating of convection drying. This should help to avoid the less dense (and more open) central region and more dense (less open) bottom region formed during convection drying from the premature drainage from the central region driven by gravity. Indeed, this can readily be observed from the SEM and Micro-CT images (See FIGS. 6a vs. 6b and FIGS. 7a vs. 7b) where it can be seen that the Microwave dried Article 27 results in a more homogenous porous structure through the thickness of the Article.

Note that any actives and/or compositions disclosed herein can be used in and/or with the articles, and in particular the household care articles, disclosed in the following U.S Patent Applications, including any publications claiming priority thereto: U.S. 61/229,981; U.S. 61/229,986; U.S. 61/229,990; U.S. 61/229,996; U.S. 61/230,000; and U.S. 61/230,004. Such articles may comprise one or more of the following: detersive surfactant; plasticizer; enzyme; suds suppressor; suds booster; bleach; bleach stabilizer; chelant; cleaning solvent; hydrotrope; divalent ion; fabric softener additive (e.g. quaternary ammonium compounds); nonionic surfactant; perfume; and/or a perfume delivery system. Such articles may be utilized in methods including, but not limited to: dosing into a washing machine to clean and/or treat fabric; dosing into a dishwasher to clean and/or treat cutlery; and dosing into water to clean and/or treat fabric and/or hard surfaces.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for preparing a flexible porous dissolvable solid structure article, comprising the steps of:
   a. preparing a pre-mixture comprising a surfactant, a water soluble polymer, and optionally a plasticizer, wherein said pre-mixture comprises:
      i. from about 15% to 50% solids; and
      ii. a viscosity of from about 2,500 cps to 150,000 cps;

b. aerating said pre-mixture by introducing a gas into the pre-mixture to form a wet aerated pre-mixture;

c. forming the wet aerated pre-mixture into one or more shapes to provide a shaped wet aerated pre-mixture; and d. drying the shaped wet aerated pre-mixture in a drying environment, wherein the drying environment is heated, such that the shaped wet aerated pre-mixture is dried within about 3 minutes to about 90 minutes to a final moisture content from about 0.1% to about 25% moisture, to a dry density of from about 0.10 g/cm$^3$ to about 0.40 g/cm$^3$, and a percent open cell content of from about 80% to about 100%, to form the flexible porous dissolvable solid structure article comprising the surfactant in an amount from 23% to about 75% by weight of the article.

2. The process of claim 1 wherein the drying step comprises a drying time from about 5 minutes to about 60 minutes, preferably from about 7 minutes to about 45 minutes.

3. The process of claim 1 further comprising a heating step of the pre-mixture before and during the aeration process wherein the pre-mixture is between about 40° C. and about 99° C.

4. The process of claim 3 wherein the pre-mixture is between about 50° C. and about 95° C.

5. The process of claim 3 wherein the pre-mixture is between about 60° C. and about 90° C.

6. The process of claim 1 further comprising the step of cutting the flexible dissolvable porous solid structure article.

7. The process of claim 1 further comprising a step of modifying the flexible dissolvable porous solid structure article wherein the modifying step is selected from the group consisting of: forming the flexible dissolvable porous solid structure article into a three dimensional structure, printing onto the surface of the flexible dissolvable porous solid structure article, texturizing the surface of the flexible dissolvable porous solid structure article, and combinations thereof.

8. The process of claim 1 wherein the drying environment is selected from the group consisting of one or more drying rooms, convection ovens, Truck/Tray driers, multi-stage inline driers, impingement ovens/driers, rotary ovens/driers, inline roasters, rapid high heat transfer ovens and driers, dual plenum roasters, conveyor driers, vacuum drying chambers and combinations thereof, such that the drying environment is between 100° C. and 150° C.

9. The process of claim 1 wherein the drying step is accomplished by Microwave Drying or Radio Frequency Drying and combinations thereof.

10. A process for preparing a porous dissolvable solid structure article, comprising the steps of:

a. preparing a pre-mixture comprising surfactant, water soluble polymer, and optionally plasticizer, wherein said pre-mixture comprises:
  i. from about 15% to 50% solids; and
  ii. a viscosity of from about 15,000 cps to 150,000 cps b. heating the pre-mixture between about 40° C. and about 99° C.;

c. aerating said pre-mixture by introducing a gas into the pre-mixture to form a wet aerated pre-mixture;

d. forming the wet aerated pre-mixture into a desired one or more shapes to provide a shaped wet aerated pre-mixture; and e. drying the shaped wet aerated pre-mixture, wherein the drying step comprises a drying time from about 3 minutes to about 90 minutes, to a dry density of from about 0.10 g/cm$^3$ to about 0.25 g/cm$^3$, and a percent open cell content of from about 80% to about 100%, to form the porous dissolvable solid structure article comprising the surfactant in an amount from 23% to about 75% by weight of the article.

11. The process of claim 10 wherein the drying step comprises a drying time from about 5 minutes to about 60 minutes.

12. The process of claim 11 wherein the drying step comprises a drying time from about 7 minutes to about 45 minutes.

13. A process for preparing a flexible porous dissolvable solid structure article, comprising the steps of:

(a) preparing a pre-mixture comprising surfactant, water soluble polymer, and optionally plasticizer, wherein said pre-mixture comprises:
  (i) from about 15% to 50% solids; and
  (ii) a viscosity of from about 15,000 cps to 150,000 cps;

(b) aerating said pre-mixture by introducing a gas into the pre-mixture to form a wet aerated pre-mixture;

(c) forming the wet aerated pre-mixture into a desired one or more shapes to provide a shaped wet aerated pre-mixture; and (d) drying the shaped wet aerated pre-mixture in a drying environment, wherein the drying step comprises a drying time from about 3 minutes to about 90 minutes, and wherein the drying environment is heated to a temperature between 100° C. and 150° C., such that the shaped wet aerated pre-mixture is dried to a final moisture content from about 0.1% to about 25% moisture, to a dry density of from about 0.10 g/cm$^3$ to about 0.25 g/cm$^3$, and a percent open cell content of from about 80% to about 100%, to form the flexible dissolvable porous solid structure article comprising the surfactant in an amount from 23% to about 75% by weight of the article.

* * * * *